(12) United States Patent
Paul et al.

(10) Patent No.: US 12,409,140 B2
(45) Date of Patent: Sep. 9, 2025

(54) THERAPEUTIC FORMULATIONS AND USES THEREOF

(71) Applicant: Bionomics Limited, Eastwood (AU)

(72) Inventors: Dharam Paul, Eastwood (AU); Julia Crossman, Eastwood (AU); Elizabeth Doolin, Eastwood (AU); Tom Reynolds, Bend, OR (US); Xiangming Wu, Bend, OR (US); Jeff Millan, Bend, OR (US); Thomas Stumpfig, Bend, OR (US); Kristie Downing, Bend, OR (US)

(73) Assignee: Bionomics Limited, Eastwood (AU)

( * ) Notice: Subject to any disclaimer, the term of this patent is extended or adjusted under 35 U.S.C. 154(b) by 635 days.

(21) Appl. No.: 17/641,020

(22) PCT Filed: Feb. 17, 2020

(86) PCT No.: PCT/AU2020/050132
§ 371 (c)(1),
(2) Date: Mar. 7, 2022

(87) PCT Pub. No.: WO2021/056048
PCT Pub. Date: Apr. 1, 2021

(65) Prior Publication Data
US 2023/0147869 A1 May 11, 2023

Related U.S. Application Data

(60) Provisional application No. 62/904,162, filed on Sep. 23, 2019.

(51) Int. Cl.
*A61K 9/20* (2006.01)
*A61K 31/5377* (2006.01)

(52) U.S. Cl.
CPC .......... *A61K 9/2054* (2013.01); *A61K 9/2095* (2013.01); *A61K 31/5377* (2013.01)

(58) Field of Classification Search
CPC .......... A61K 9/20; A61K 9/204; A61K 9/205; A61K 9/2054; A61K 9/2095; A61K 31/4164; A61K 31/415; A61K 31/41; A61K 31/381
See application file for complete search history.

(56) References Cited

U.S. PATENT DOCUMENTS

| | | | |
|---|---|---|---|
| 2003/0045563 A1* | 3/2003 | Gao | A61K 31/415 514/602 |
| 2011/0236487 A1* | 9/2011 | Shaw | A61P 25/20 977/775 |
| 2013/0084332 A1* | 4/2013 | Folger | A61K 9/2893 514/212.07 |

FOREIGN PATENT DOCUMENTS

WO WO-2008046135 A1 * 4/2008 ......... A61K 31/4375

OTHER PUBLICATIONS

Zheng et al (Effects of HPMCAS on recrystallization inhibition of nimodipine solid dispersions prepared by hot-melt extrusion and dissolution enhancement of nimodipine tablets, Colloids and Surfaces B: Biointerfaces 172, 2018) (Year: 2018).*
"International Search Report"; prepared for PCT/AU2020/050132; authorized officer Padraig Fyfe; Apr. 1, 2020; 6 pages.

* cited by examiner

*Primary Examiner* — Micah Paul Young
(74) *Attorney, Agent, or Firm* — WINSTEAD PC

(57) ABSTRACT

This invention relates to formulations of compound (I) (BNC210), an allosteric modulator of the α7-nicotinic receptor with non-sedative anxiolytic effects; specifically, solid dispersions, methods of manufacture thereof, and therapeutic methods and uses in the treatment of diseases of the central nervous system thereof.

15 Claims, 11 Drawing Sheets

THERAPEUTIC FORMULATIONS AND USES THEREOF

FIELD

Figure 1:
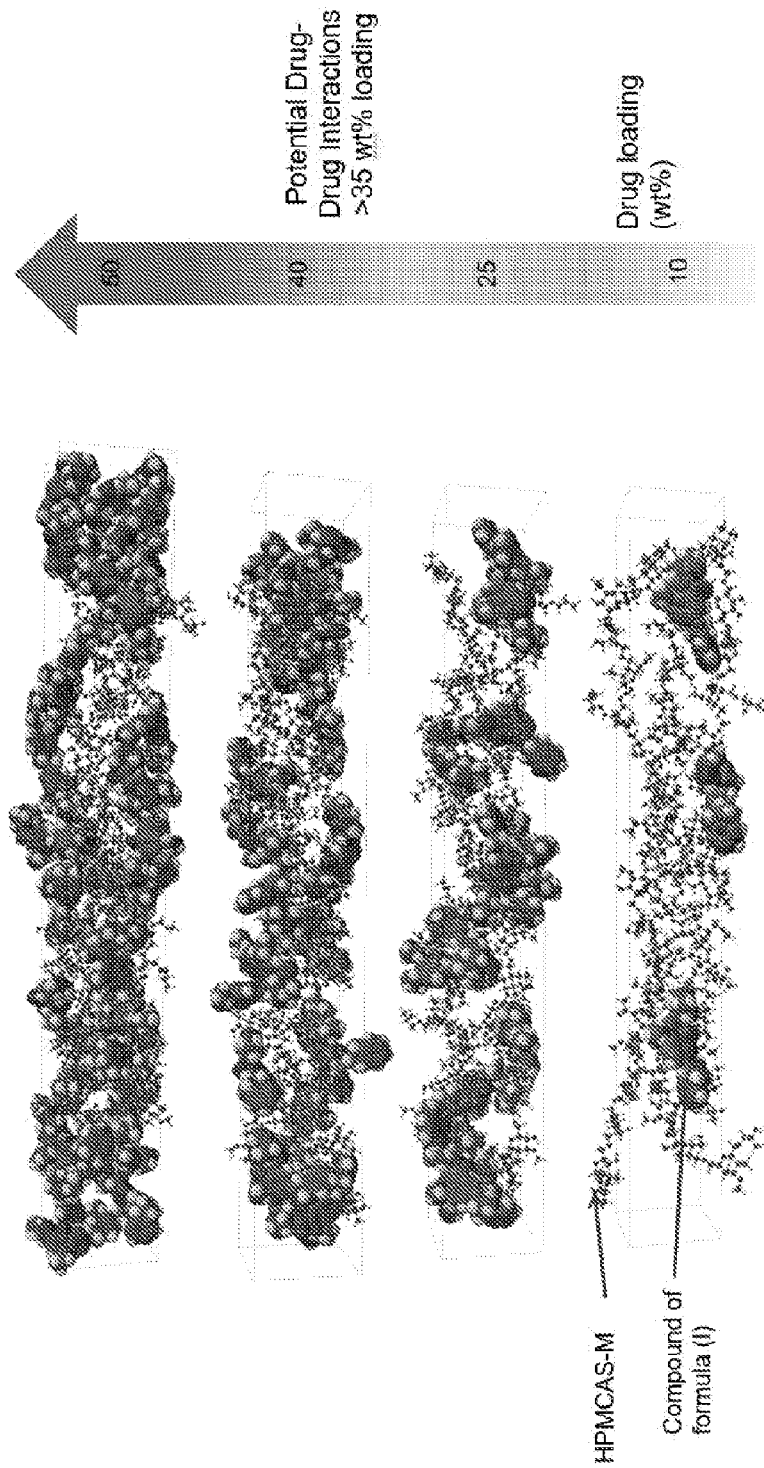

This invention relates generally to therapeutic formulations comprising a therapeutic compound which exhibits non-sedative anxiolytic effects, the manufacture of said formulations, and methods and uses of said formulations in treating anxiety and related diseases of the central nervous system.

BACKGROUND

Formulation science is a complex but very important aspect of creating physiologically effective medicines which ensures that the active pharmaceutical ingredient (API) is delivered to the required part of the body, in the right concentration and rate to enable an effective therapeutic response while also avoiding any undesirable side effects. There are literally thousands of excipients/ingredients for a formulator to choose from in order to facilitate the desired effect, and this is quite dependant on the physical properties and desired pharmacokinetics (PK) of the API.

In addition to the above, the specific form of the formulation whether it be oral (e.g., capsule, tablet, etc.), parental (e.g., intravenous, subcutaneous, intramuscular, etc.) or topical (e.g., cutaneous, ointments, etc.) are also important factors to consider when formulating a particular API.

For instance, in relation to oral delivery whether it be capsule or tablet, preformulation studies are imperative in order to better understand the API's physical, chemical and mechanical properties. Such formulation studies consider factors such as pH, solubility, particle size, polymorphism and so on which ultimately influences bioavailability and hence the activity of a API when formulated.

Another factor to consider in relation to bioavailability is the effect of administering a formulation to a patient on an empty stomach vs a non-empty stomach. Thus food effect studies or food effect bioavailability (BA) are typically conducted to assess the effects of food on the rate and extent of absorption of a formulation containing the API when the formulation is administered shortly after a meal (fed conditions) when compared to administration under fasting conditions.

The present invention seeks to alleviate some of the shortcomings of formulations of a known non-sedative anxiolytic API.

SUMMARY OF THE INVENTION

In an aspect the invention provides a solid dispersion comprising a compound of formula (I):

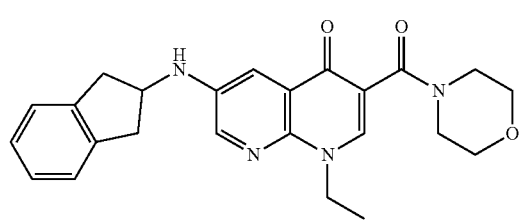 [SMILES: CCn1cc(C(=O)N2CCOCC2)c(=O)c2cc(NC3Cc4ccccc4C3)cnc21]

(I)

or a salt, or prodrug thereof;
dispersed within a polymer matrix formed by at least one pharmaceutically acceptable polymer.

The present invention also provides solid dosage formulations and specifically tablet formulations comprising said solid dispersion.

The present invention also provides solid dosage formulations and specifically tablet formulations comprising said solid dispersion which are prepared by dry granulation and compression.

In certain embodiments the at least one pharmaceutically acceptable polymer is an at least one crystallisation inhibitor polymer.

In a further embodiment the solid dispersion comprises an effective amount of (i) a compound of formula (I) or a salt or prodrug thereof, and (ii) an amount of at least one crystallisation inhibitor polymer wherein the ratio of (i):(ii) is from about 10:90 to about 80:20 (wt/wt %).

During preformulation studies the inventors noted that compounds of formula (I) displayed a high melting point, poor in vitro solubility of the crystalline form of compound I (which is thermodynamically stable form and observed when the amorphous form of compound I is exposed to water/moisture), and low oral exposure which increased with the addition of 0.5% HPMC to suspension formulations and depend upon fed/fasted state of subject. In this regard it was observed that there was a need to develop an alternative formulation for further development focusing on preventing (or at least substantially minimising) the formation of poorly soluble crystalline forms, reducing the food effect and increasing oral exposure. Solid dispersion technologies, such as hot melt extrusion (HME) and spray drying, lipid formulations and nanosizing were considered as approaches to overcome these formulation deficiencies. Considering the targeted dose of the compound and good solubility in mixture of dichloromethane (DCM) and methanol, it was recognised by the inventors that compounds of formula (1) may be suitable for spray drying. The undesirable drug/drug interactions which lead to crystallisation have been shown to be avoided when certain crystallisation inhibitor polymers are used in spray-dried amorphous solid dispersions of the drug (compound of formula (I)) which can be used, for instance, in the preparation of tablets (see FIG. 1). The preferred ratio of compounds of formula (I):polymer are discussed below, and can lead to advantageously high loading of the API in a subsequent tablet formulation. These resultant tablet formulations are shown to display good in vivo solubility and avoid or at least minimise any adverse food effect.

In a further aspect the invention provides a tablet formulation prepared from a solid dispersion comprising a compound of formula (I):

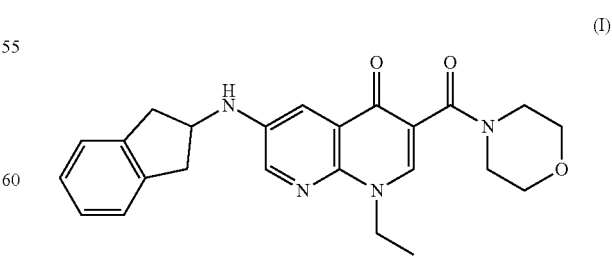

(I)

or a salt, or prodrug thereof;
dispersed within a polymer matrix formed by a pharmaceutically acceptable polymer.

In a further aspect, the invention provides a tablet comprising:

(i) 5 mg-500 mg of a compound of formula (I):

(I)

or a salt, or prodrug thereof; and (ii) a crystallization inhibitor polymer;

wherein the ratio of (i):(ii) is from about 10:90 to about 80:20 (wt/wt %).

In another aspect the invention provides a solid dispersion comprising:

(i) a compound of formula (I):

(I)

or a salt, or prodrug thereof; and (ii) a crystallization inhibitor polymer;

wherein the ratio of (i):(ii) is from about 10:90 to about 80:20 (wt/wt %).

In a further aspect the invention provides a method of treating a disease of the central nervous system including the step of administering to a subject in need thereof an effective amount of a tablet prepared from a solid dispersion comprising a compound of formula (I) in substantially amorphous form:

(I)

or a salt, or prodrug thereof;

dispersed within a polymer matrix formed by a pharmaceutically acceptable polymer.

In another aspect the invention provides a method of treating a disease of the central nervous system including the step of administering to a subject in need thereof an effective amount of a tablet comprising:

(i) 5 mg-500 mg of a compound of formula (I) in substantially amorphous form:

(I)

or a salt, or prodrug thereof; and (ii) a crystallization inhibitor polymer;

wherein the ratio of (i):(ii) is from about 10:90 to about 80:20 (wt/wt %).

In a further aspect the invention provides the use of a tablet prepared from a solid dispersion comprising a compound of formula (I) in substantially amorphous form:

(I)

or a salt, or prodrug thereof;

dispersed within a polymer matrix formed by a pharmaceutically acceptable polymer, for treating a disease of the central nervous system.

In another aspect the invention provides the use of a tablet comprising:

(i) 5 mg-500 mg of a compound of formula (I) in substantially amorphous form:

(I)

or a salt, or prodrug thereof; and (ii) a crystallization inhibitor polymer;

wherein the ratio of (i):(ii) is from about 10:90 to about 80:20 (wt/wt %), for treating a disease of the central nervous system.

In still a further aspect the invention provides the use of a solid dispersion formulation comprising:
(i) 5 mg-500 mg of a compound of formula (I) in substantially amorphous form:

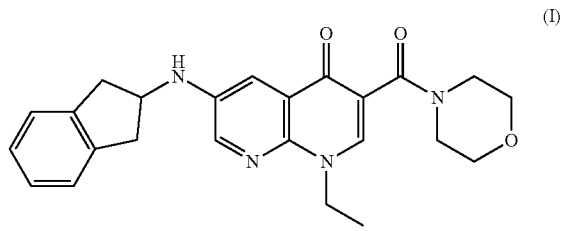 [SMILES: CCn1cc(C(=O)N2CCOCC2)c(=O)c2cc(NC3Cc4ccccc4C3)cnc21]

(I)

or a salt, or prodrug thereof; and
(ii) a crystallization inhibitor polymer;
wherein the ratio of (i):(ii) is from about 10:90 to about 80:20 (wt/wt %),
in the manufacture of a medicament in the form of a tablet, for the treatment of a disease of the central nervous system.

BRIEF DESCRIPTION OF THE DRAWINGS/FIGURES

FIG. 1 is graph depicting a 3-D representation of the interaction between HPMCAS-M and compound of formula (I) ("BNC210") relative to drug loading.

Figure 2A:
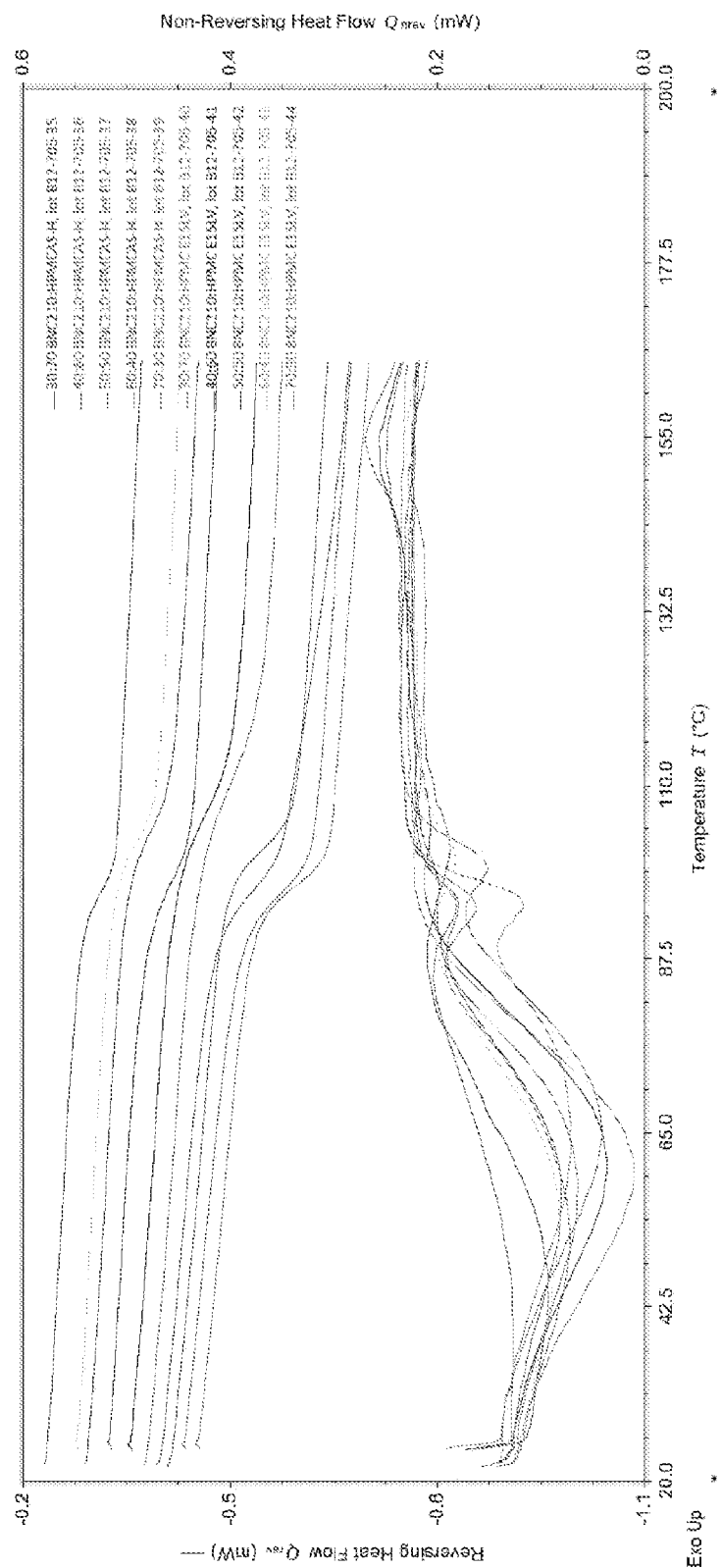

FIG. 2a: is a graph depicting mDSC of spray dried compositions of the present invention (reversing heat flow vs temp).

Figure 2B:
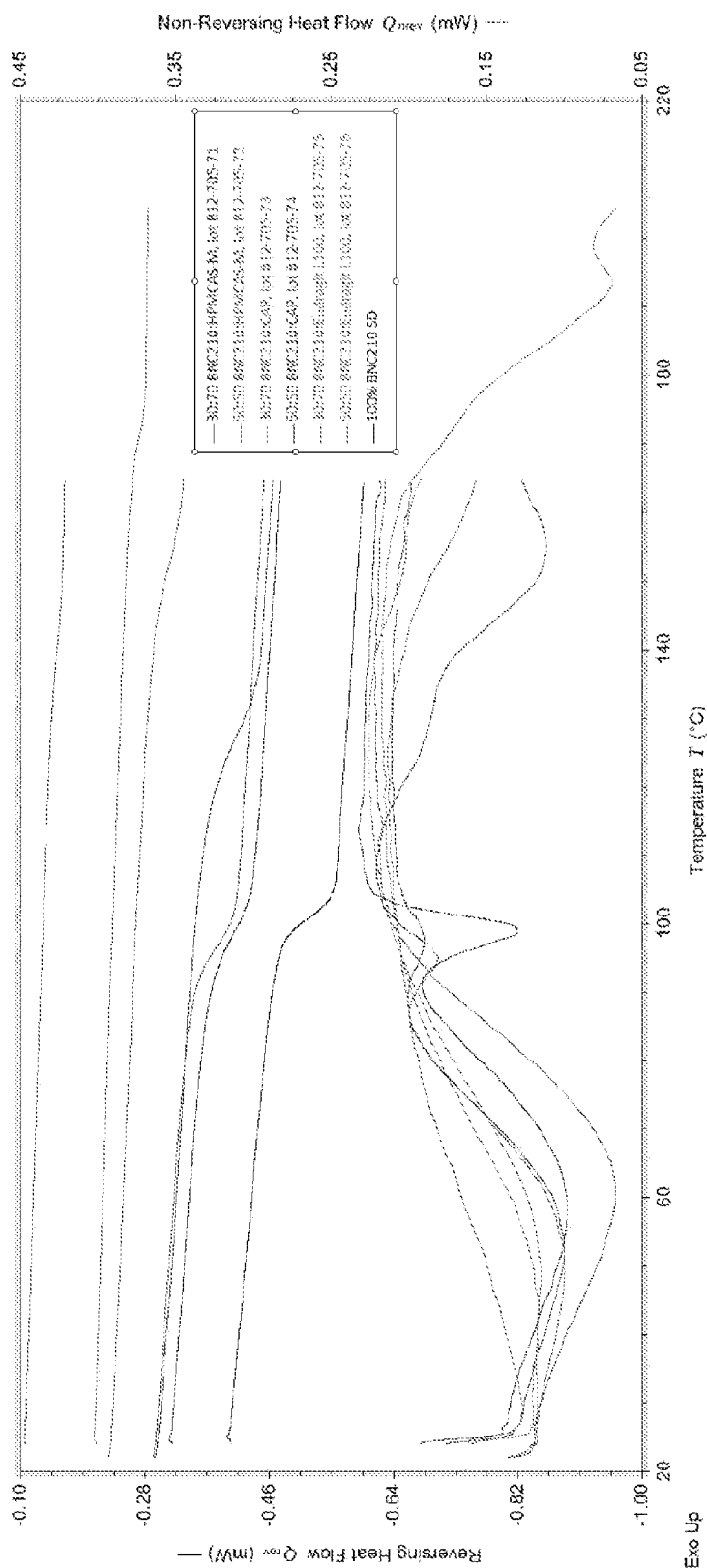

FIG. 2b: is a graph depicting mDSC of spray dried compositions of the present invention (reversing heat flow vs temp).

Figure 2C:
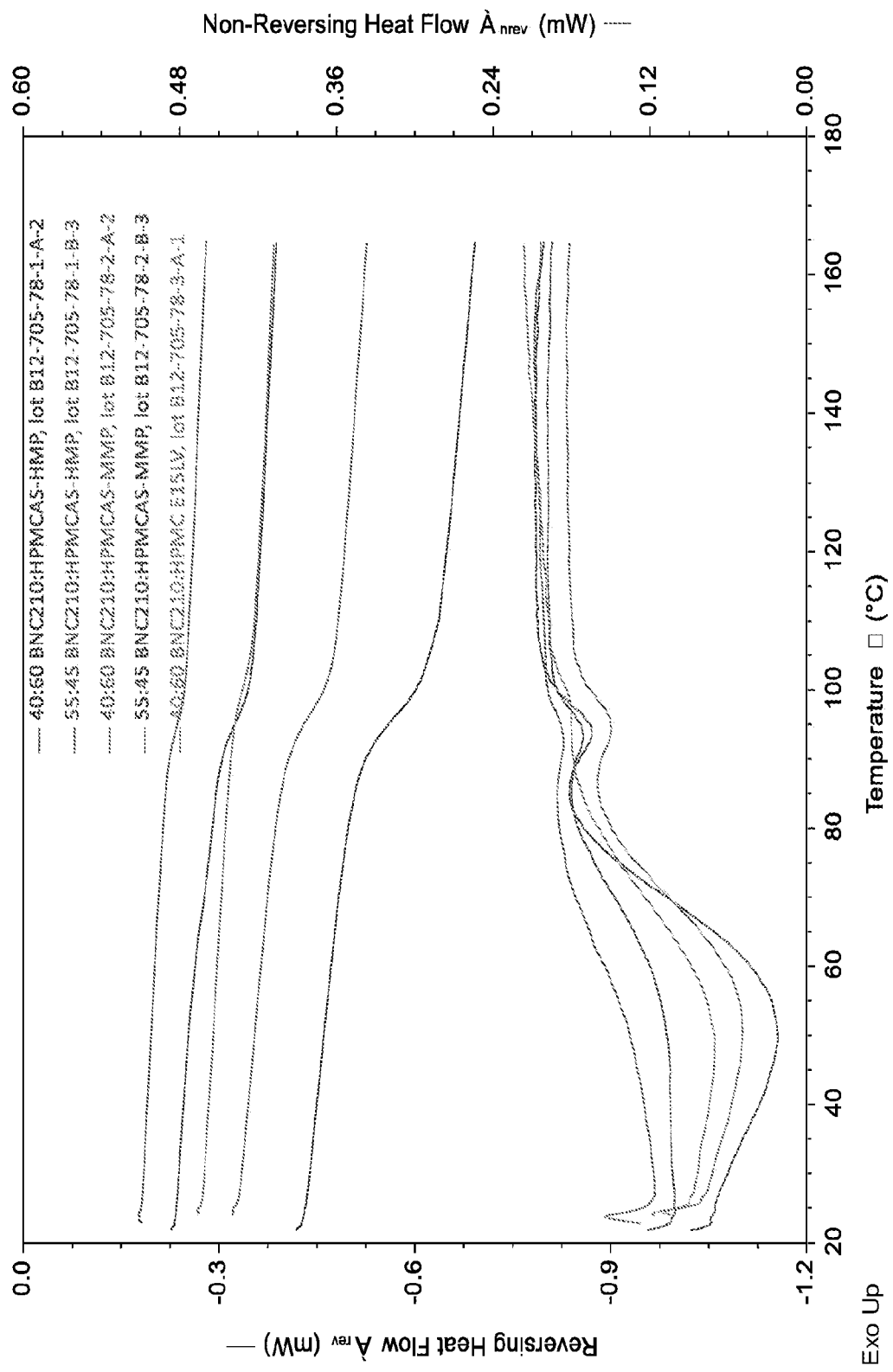

FIG. 2c: is a graph depicting mDSC of spray dried compositions of the present invention (reversing heat flow vs temp).

Figure 3A:
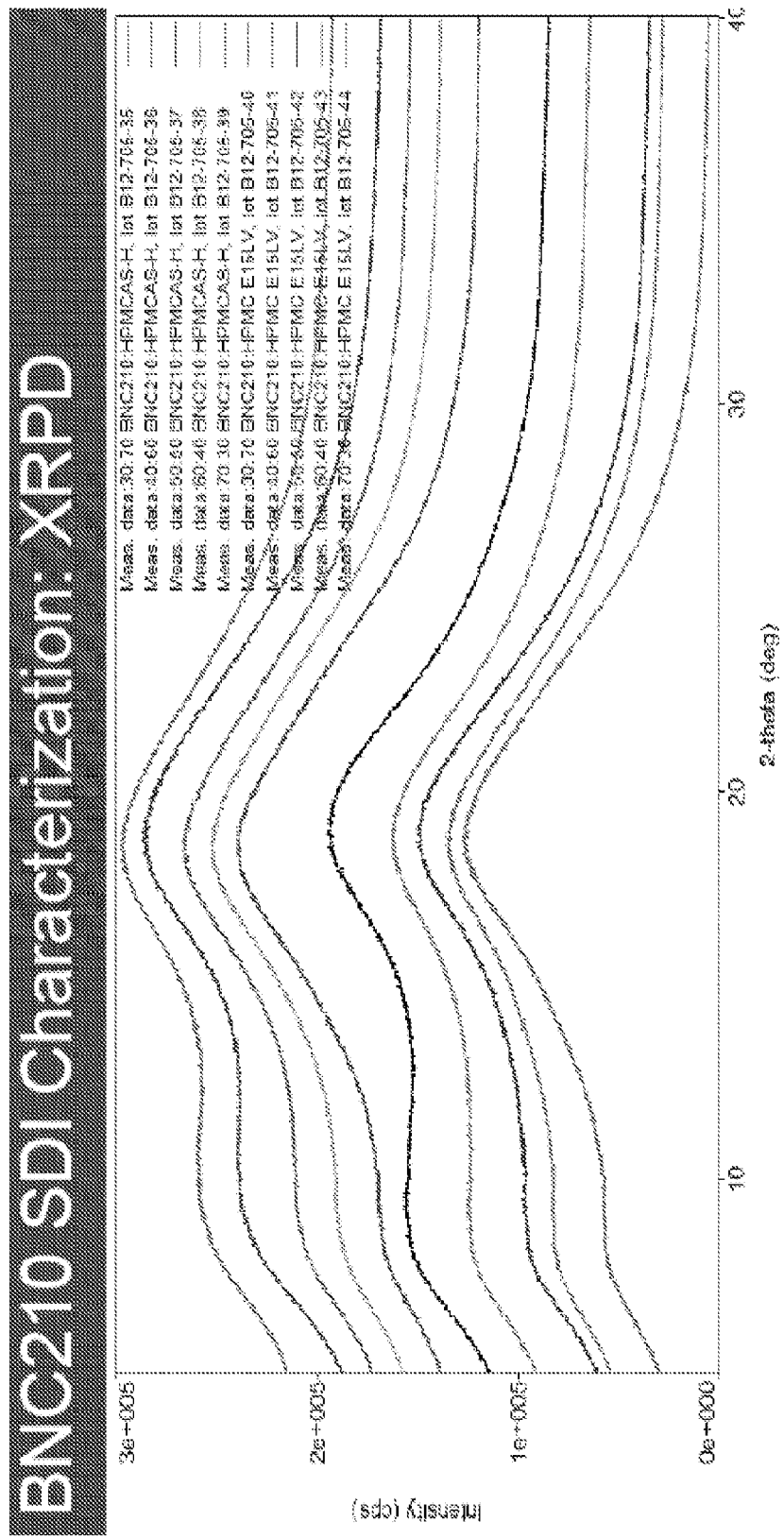

FIG. 3a: is a graph depicting XRPD characterisation of spray dried compositions of the present invention (intensity (cps) vs 2-theta (deg)).

Figure 3B:
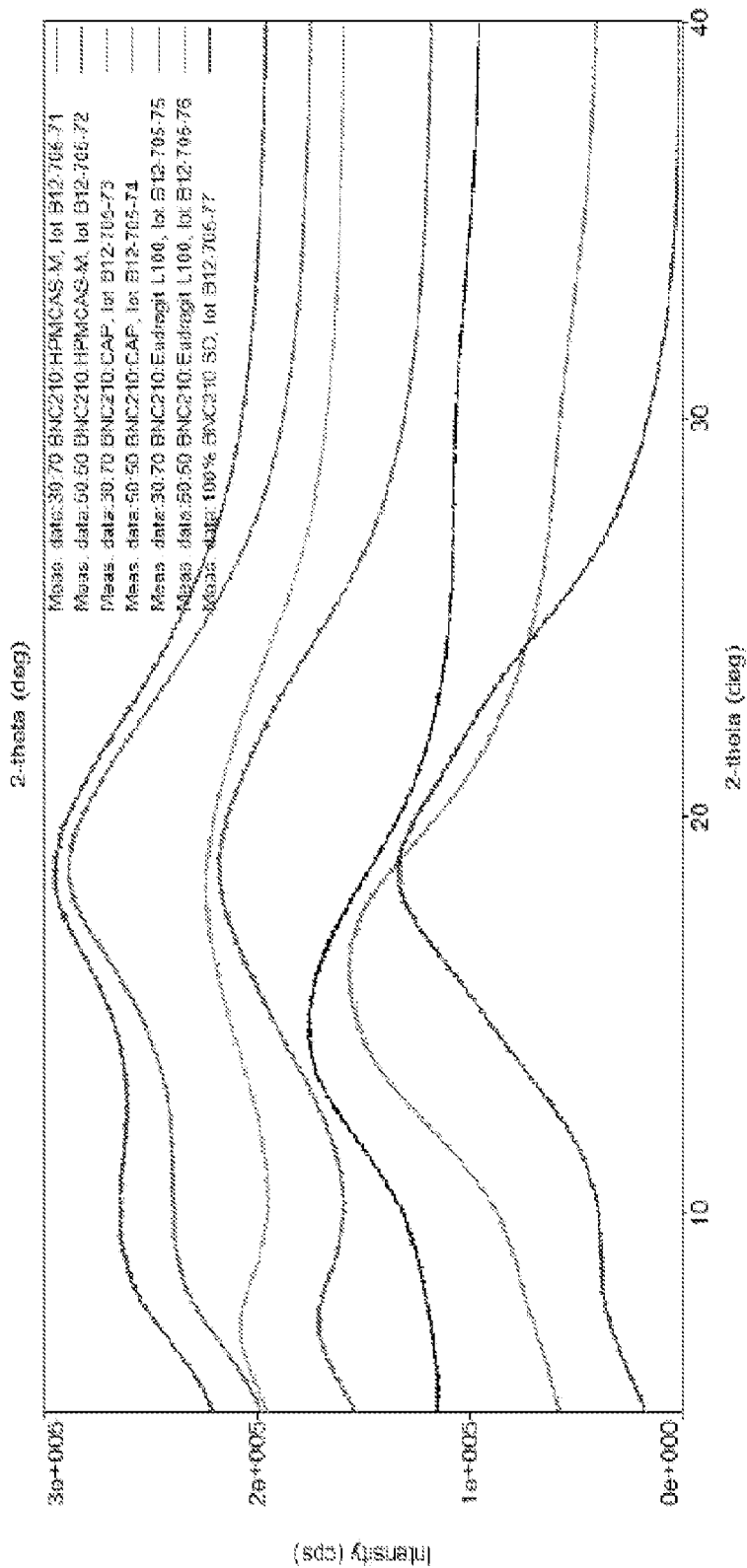

FIG. 3b: is a graph depicting XRPD characterisation of spray dried compositions of the present invention (intensity (cps) vs 2-theta (deg)).

Figure 3C:
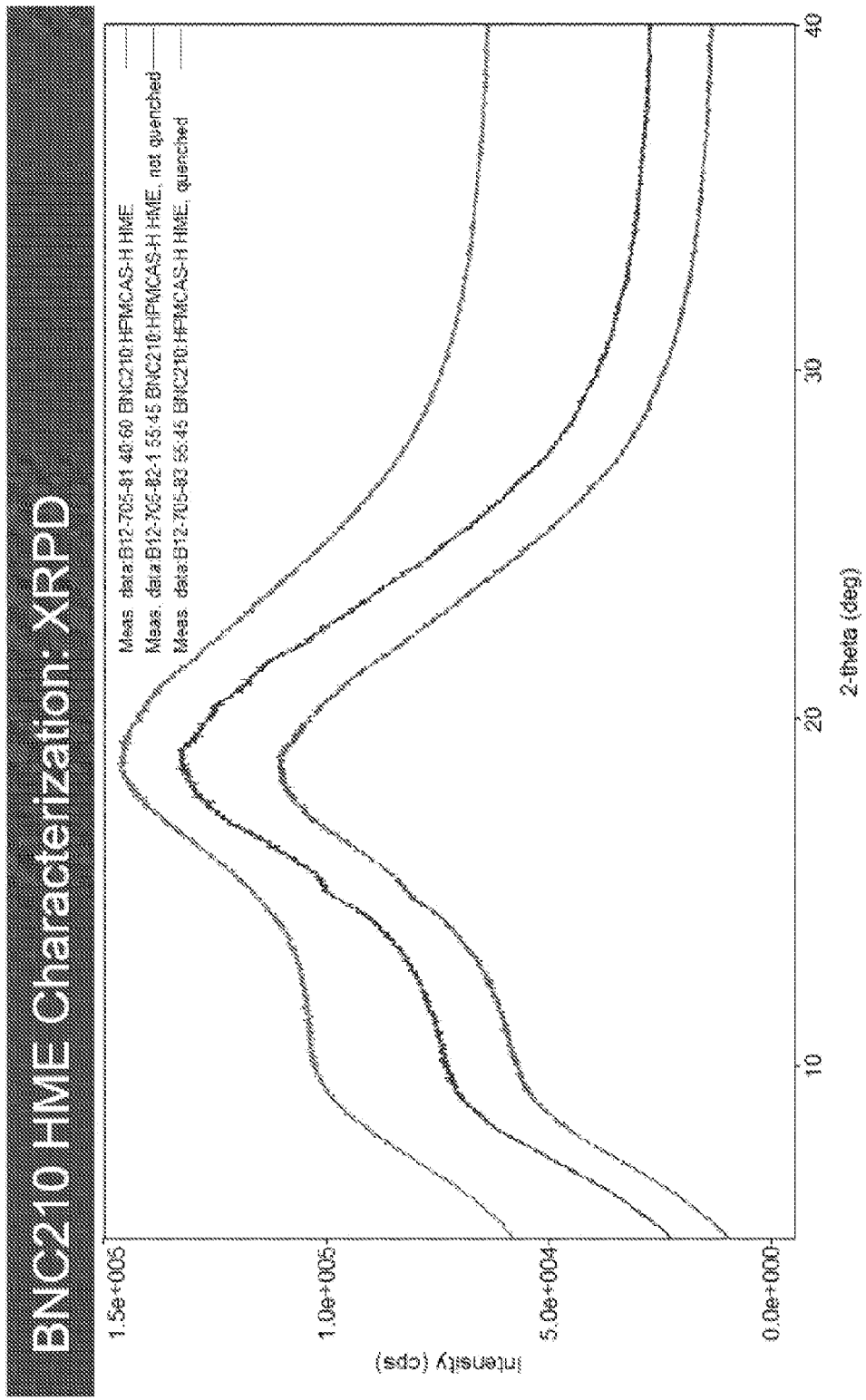

FIG. 3c: is a graph depicting XRPD characterisation of spray dried compositions of the present invention (intensity (cps) vs 2-theta (deg)).

Figure 4A:
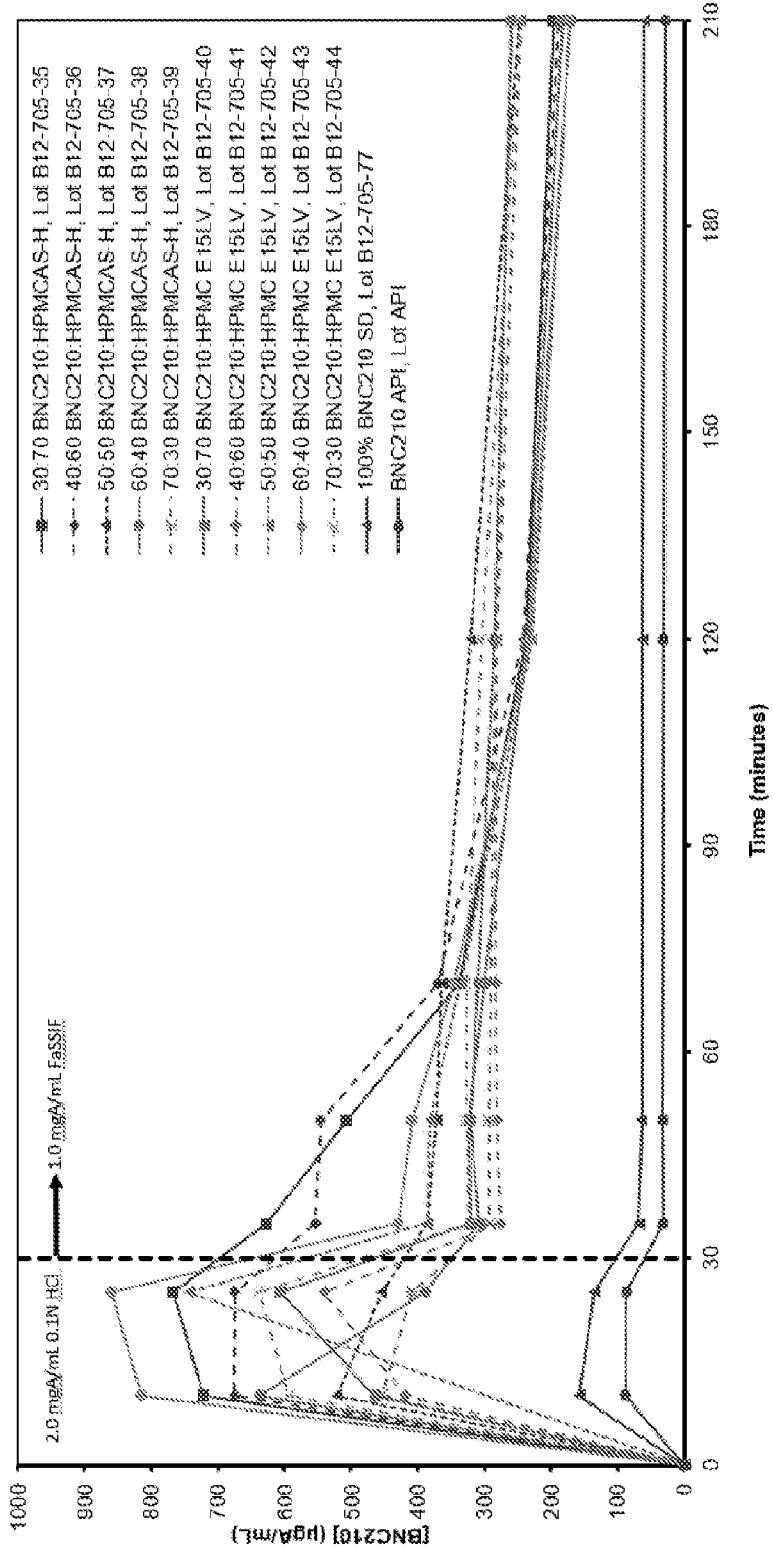

FIG. 4a: is a graph depicting the results of spray dried dispersions dissolution time testing (API (BNC210) (μgA/mL) vs time (mins)).

Figure 4B:
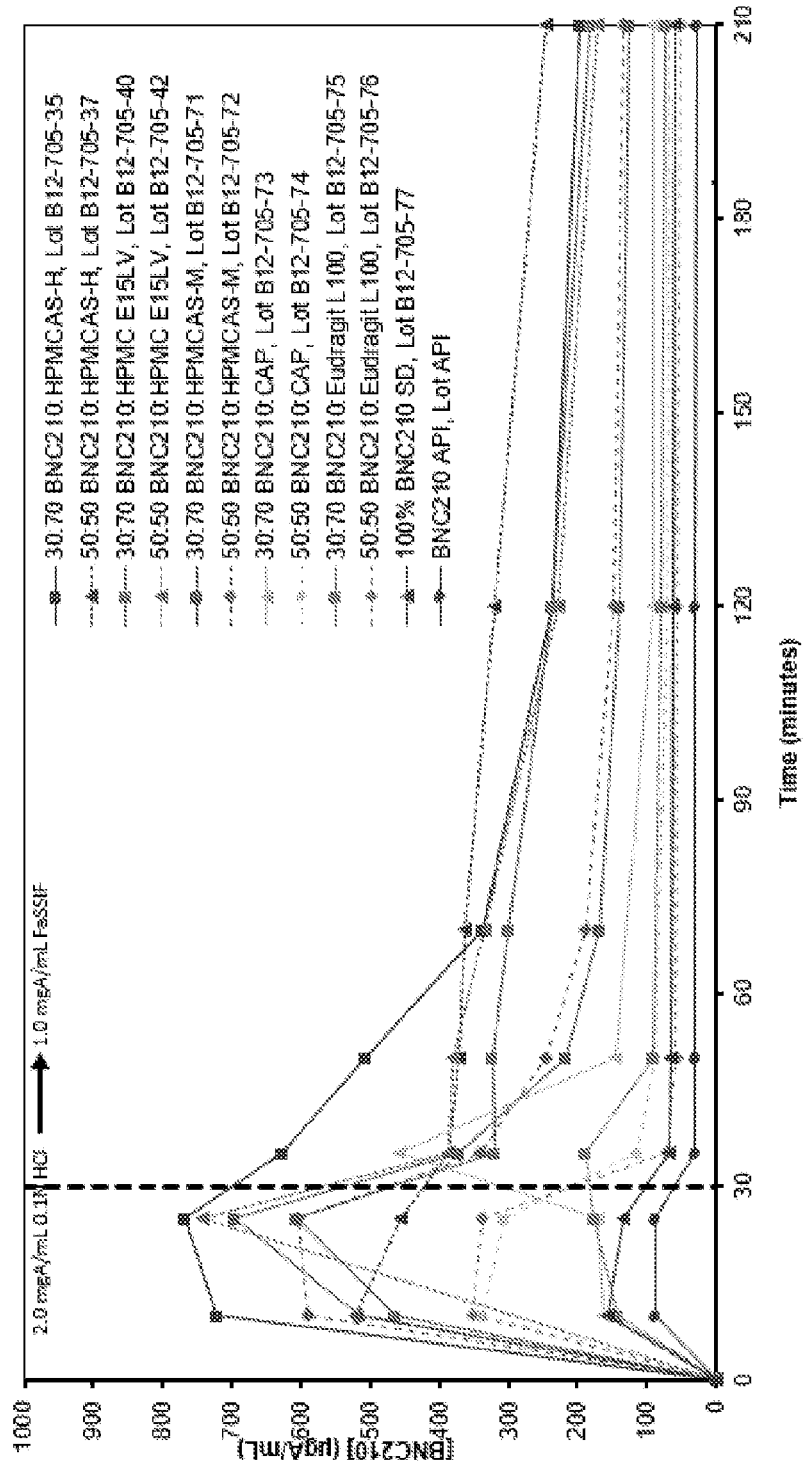

FIG. 4b: is a graph depicting the results of spray dried dispersions dissolution time testing (API (BNC210) (μgA/mL) vs time (mins)).

Figure 4C:
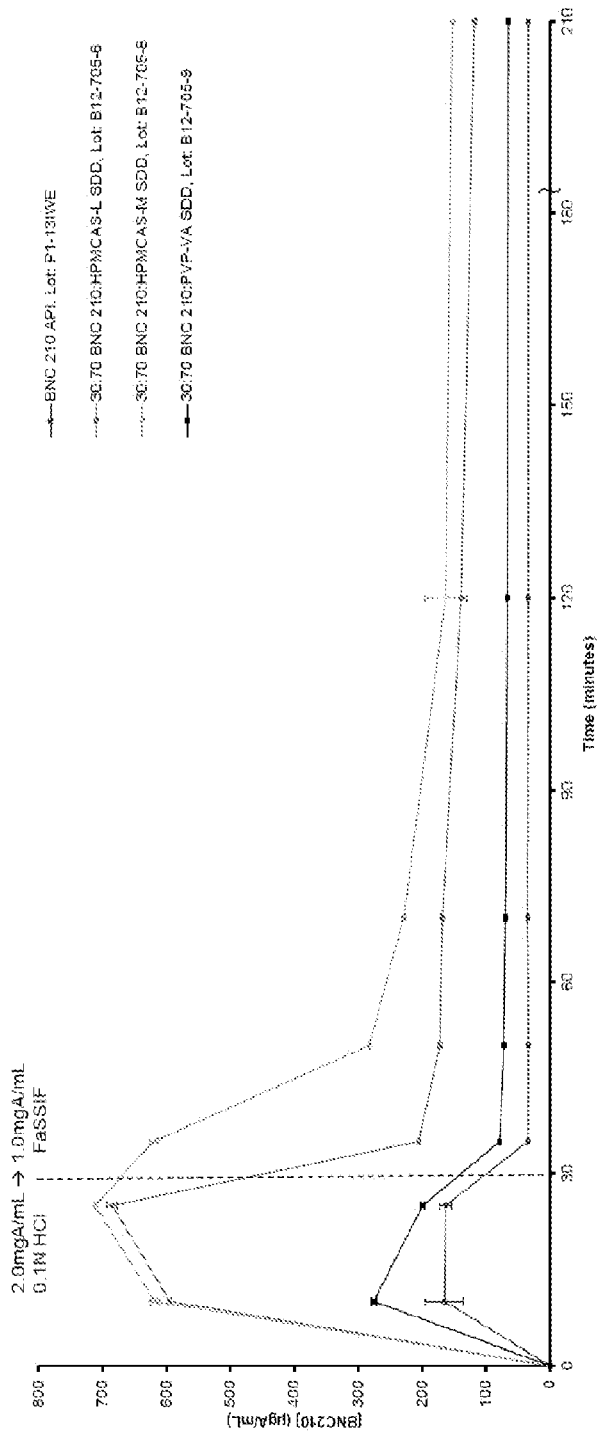

FIG. 4c: is a graph depicting the results of spray dried dispersions dissolution time testing (API (BNC210) (μgA/mL) vs time (mins)).

Figure 4D:
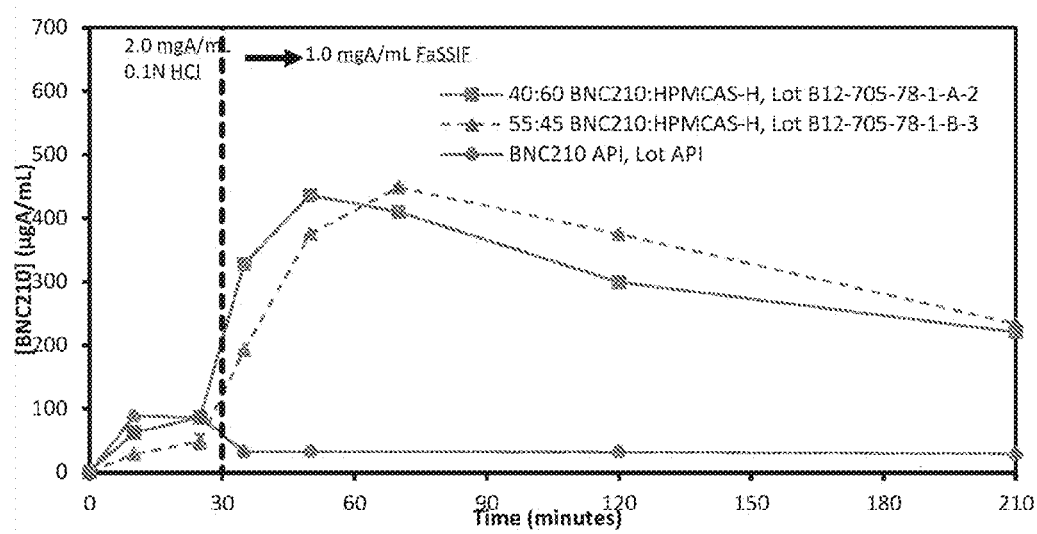

FIG. 4d: is a graph depicting the results of hot melt extrusion dissolution time testing (API (BNC210) (μgA/mL) vs time (mins)).

Figure 4E:
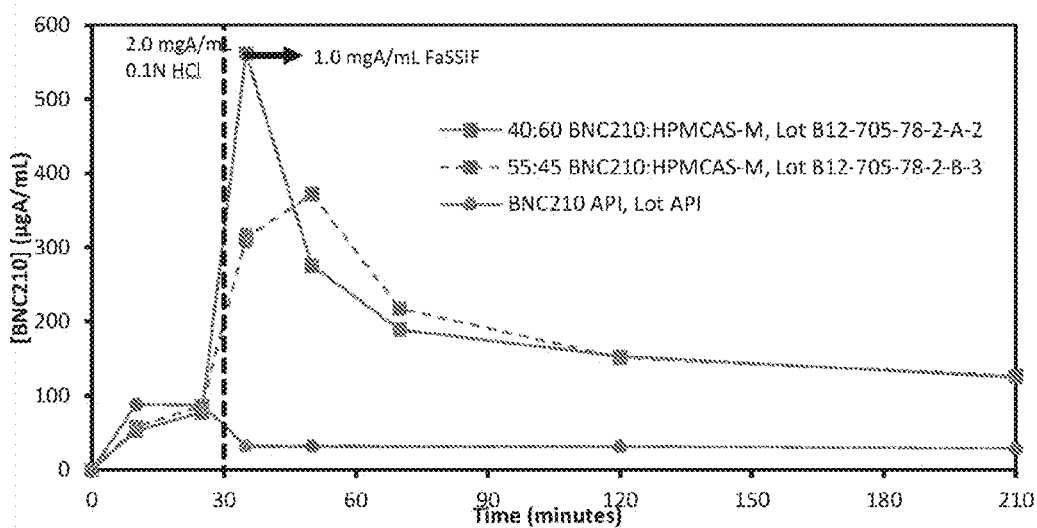

FIG. 4e: is a graph depicting the results of hot melt extrusion dissolution time testing (API (BNC210) (μgA/mL) vs time (mins)).

DETAILED DESCRIPTION OF THE INVENTION

Unless defined otherwise, all technical and scientific terms used herein have the same meaning as commonly understood by those of ordinary skill in the art to which the invention belongs. For the purposes of the present invention, the following terms are defined below.

"BNC210" refers to compound of formula (I) as depicted below:

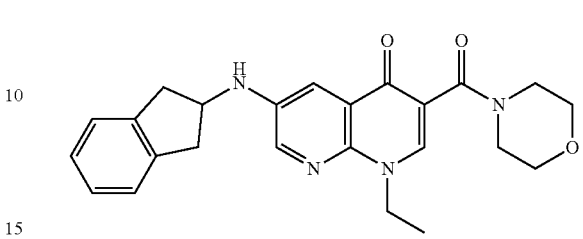

This compound and salts thereof can be prepared as defined in PCT/AU2007/001566 (WO 2008/046135) the entire contents being incorporated herein by reference.

"Excipients" are pharmaceutically inactive substances that serve as the vehicle or medium for a drug or other active substances, the "crystallisation inhibitor polymers" described herein are separate from the use of the term "excipients" as used herein. Accordingly, the invention, in certain embodiments, contemplates compositions with BNC210, at least one crystallisation inhibitor polymer and one or more excipients.

"HPMC" is the excipient hydroxypropyl methylcellulose, also known as hypromellose. It is a semisynthetic, inert, viscoelastic polymer. It is a non-ionic, hydrophilic derivative of cellulose ether and is stable over pH range 3-11. One preferred example is HPMC E15 LV, a premium polymer of low viscosity grade of about 15 cP (sold as METHCEL™ E15 Industrial LV from Dupont).

"HPMCAS" is the excipient hydroxypropyl methylcellulose acetate succinate (or hypermellose acetate succinate) and is primarily used for enteric coating materials for both regular enteric coating and sustained release formulations with various contents of acetyl and succinoyl groups in the polymer. There are several types of HPMCAS, which dissolve at different pH levels. Type L HPMCAS represents polymer with high ratio of succinoyl substituting to acetyl substitution (S/A ratio) while type H with low S/A ratio and type M with medium S/A ratio with a higher S/A ratio. Type L HPMCAS dissolves at lower pH (≥5.5), compared with pH≥6.0 for type M and pH≥6.8 for type H.

"Cellulose-microcrystalline" is an excipient and is often referred to as refined wood pulp, often used as a texturiser, an anti-caking agent, suspending agent and adsorbent. Often sold as microcrystalline cellulose under the tradename Avicel PH-105.

"Croscarmellose sodium" or "sodium croscarmellose" is an internally linked sodium salt of carboxymethylcellulose and is used as a superdisintergrant. It is sold by, inter alia, FMC Biopolymer under the tradename of Ac-Di-Sol SD 711.

"Colloidal Silica" (also silicon dioxide or colloidal silicon dioxide) is used in tablet preparations as an anti-caking agent, adsorbent, disintergrant or a glidant to allow improved flowability when tablets are processed. It is sold by, inter alia, Cabot under the tradename Cab-O-Sil MP.

"Sodium stearyl fumurate" (also known as sodium monostearyl fumurate or sodium monooctadecyl fumurate) is a water-soluble lubricant for aiding tablet compression. It is sold by, inter alia, JRS Pharma under the tradename Pruv SSF.

"PVP-VA" (also PVP/VA copolymer or Poly(l-vinylpyrrolidone-co-vinyl) Acetate, or Copovidone, or PVP VA64) is a vinylpyrrolidone-vinyl acetate copolymer (vinyl acetate-vinyl pyrrolidone copolymer) of random linear arrangement produced by the free radical polymerisation of the monomers in ratios varying from 70:30 to 30:70 vinyl acetate to vinyl pyrrolidone. Also known under the tradenames Polectron 845 and Luviskol VA 281, Kolima 10, 35, Ganhon S 860, or Ganex E313, just to name a few.

"CAP" (also referred to as Cellacetate, Cellacefate, Celluloseacetate, 1,2-benzenedicarboxylate) is a cellulose acetate phthalate polymer which is insoluble in water, alcohols, hydrocarbons and chlorinate hydrocarbons. Often used as an enteric coating material.

"Eudragit" is the common tradename of copolymers derived from esters of acrylic and methacrylic acids containing ratio ranges from two to three methacrylate monomers, such as metharylic acid, methacrylic acid esters and dimethylaminomethyl methacrylate.

Soluplus™ is a polyvinyl caprolactam-polyvinyl acetate polyethylene glycol graft copolymer (PCL-PVAc-PEG), available from BASF. It is a water soluble copolymer with average molecular weight ranging from 90,000 to 140,000 g/mol, and is capable of solubilizing poorly water soluble drugs.

In the present formulation, the main active ingredient is the compound of formula (I), or a salt or prodrug thereof. The amount of the compound of formula (I) included in the formulation is effective to provide a therapeutic plasma concentration in a subject for up to 24 h. In an embodiment, the formulation when presented as a tablet comprises between about 10 mg to about 400 mg of active ingredient. In an embodiment, the formulation when presented as a tablet comprises between about 30 mg to about 300 mg of active ingredient. In an embodiment, the formulation when presented as a tablet comprises between about 50 mg to about 200 mg of active ingredient. In another embodiment, the tablet formulation comprises about 50 mg to 175 mg of active ingredient. In another embodiment, the tablet formulation comprises about 50 mg to 150 mg of active ingredient. In another embodiment, the tablet formulation comprises about 50 mg to 125 mg of active ingredient. In another embodiment, the tablet formulation comprises about 50 mg to 100 mg of active ingredient. In another embodiment, the tablet formulation comprises about 50 mg to 70 mg of active ingredient.

It will be appreciated that the solid dispersion formulation as disclosed herein comprises only the compound of formula (I) and the at least one pharmaceutically acceptable polymer or at least one crystallisation inhibitor polymer. This solid dispersion will be ultimately mixed with further excipients prior to tablet formation and such formulations (ie solid-dispersion and added excipients) are referred to herein as a pre-tabletting formulations.

For instance, a 1 gram tablet provided for by the present invention may comprise 50% of the solid dispersion and 50% of other excipients (on a % wt/% wt basis) which will be discussed further herein. It will also be appreciated that for a 1 g tablet which contains 150 mg of a compound of formula (I) one would calculate that 50% of the tablet is made up of the 50% wt/50% wt solid dispersion/excipient mixture and the solid dispersion has 30% wt of Compound (I).

The tablet formulation of the present invention will thus also comprise of a combination of formulation excipients which allows for immediate release of the active ingredient throughout the gastrointestinal tract. This can be achieved via a rapid dissolution controlled process, by swelling under the influence of a media and erosion of the matrix to release the active ingredient. In certain embodiments the formulations disclosed herein are immediate release formulations, for instance displaying about 70% dissolution in the first 15 minutes.

The solid dispersion, pre-tableting and tablet formulations discussed herein comprise an effective amount of a compound of formula (I) dispersed within a polymer matrix formed by at least one pharmaceutically acceptable polymer or crystallization inhibitor polymer (used interchangeably) to ensure retention of the compound of formula (I) in substantially amorphous form.

In certain embodiments the ratio of (i):(ii) is about 10:90, 15:85, 20:80, 25:75, 30:70, 35:65, 40:60, 45:55, 50:50, 55:45, 60:40, 65:35, 70:30, 75:25, and about 80:20 wt/wt %.

In certain embodiments the crystallisation inhibitor polymer is a polymer excipient selected from the group consisting of HPMCAS-M, HPMCAS-L, HPMCAS-H, PVP-VA, HPMC (for instance HPMC EISLV) and Soluplus.

In certain embodiments the crystallisation inhibitor polymer is HPMCAS-H.

In certain embodiments the crystallisation inhibitor polymer is HPMCAS-M.

In certain embodiments the crystallisation inhibitor polymer is HPMC Ely LV.

In certain embodiments the crystallisation inhibitor polymer is HPMCAS-L.

In certain embodiments the crystallisation inhibitor polymer is PVP-VA.

In an embodiment the solid dispersion formulations disclosed herein are produced by spray drying. In an embodiment the total weight of solids (wt % total solids) in the spray dried solution is between 2-15% wt, such as between about 2-10% wt.

In certain embodiments the spray drying solvent comprises dichloromethane.

In certain embodiments the spray drying solvent comprises dichloromethane and methanol.

In certain embodiments the spray drying solvent comprises dichloromethane and methanol in a weight to weight ratio of about 90:10 to 60:10 such as about 85:15, 80:20, 75:25, 70:30, and about 65:35 wt/wt %.

In certain embodiments the spray dried dispersion yield is from about 50-100%.

In an embodiment the solid dispersion formulations disclosed herein are produced by hot melt extrusion (HME). In certain embodiments the extrudate is produced at a temperature of about 160-190° C.

The pre-tabletting and tablet formulation may also comprise microcrystalline cellulose which is known in the art to be purified, partly depolymerised cellulose prepared by treating α-cellulose, obtained as a pulp from plant materials with mineral acids. In an embodiment, the tablet formulation or pre-tabletting formulation comprises between about 30% to about 60% (% wt/wt, based on total weight of the tablet) of microcrystalline cellulose. In another embodiment, the tablet or pre-tabletting formulation comprises about 35% to about 55% (% wt/wt) of microcrystalline cellulose. In another embodiment, the pre-tabletting and tablet formulation comprises about 40% to about 50% (% wt/wt) of microcrystalline cellulose.

In an embodiment, the pre-tabletting and tablet formulation comprises between about 0.2% to about 2% (% wt/wt, based on total weight of the tablet) of sodium stearyl fumurate (SSF). In another embodiment, the pre-tabletting and tablet formulation comprises about 0.3% to 1.5% (% wt/wt) of SSF. In another embodiment, the pre-tabletting and tablet formulation comprises about 0.5% to 1% (% wt/wt) of SSF. In another embodiment, the formulation comprises about 0.5% to 0.8% (% wt/wt) of SSF.

In other embodiments, the pre-tabletting and tablet formulation comprises about 0.8% to 2.5% (% wt/wt), based on total weight of the tablet, of croscarmellose sodium. In another embodiment, the pre-tabletting and tablet formulation comprises about 1% to 2% (% wt/wt) of croscarmellose sodium. In another embodiment, the pre-tabletting and tablet formulation comprises about 1.2% to 1.8% (% wt/wt) of croscarmellose sodium.

In other embodiments, the pre-tabletting and tablet formulation comprises between about 0.5% to about 2% (% wt/wt, based on total weight of ferrous sulphate) of colloidal silica. In another embodiment, the pre-tabletting and tablet formulation comprises about 0.7% to about 1.5% (% wt/wt) of colloidal silica. In another embodiment, the formulation comprises about 0.9% to about 1.3% (% wt/wt) of colloidal silica.

In certain embodiments the tablet formulation involves a coated tablet. Accordingly, the coating ingredients may comprise a polymer, plasticiser and pigment mixed together and dispersed finely as a film over the tablet to protect the tablet, maintain the shape of the tablet, aid in swallowing and for a lustre appearance. In the above formulations, poly(vinyl alcohol) (PVA) based coating formulations are used.

In other embodiments and to further aid in solubility, the formulations also comprise a surfactant selected from SLS (sodium lauryl sulfate) or sorbates. When added the surfactant is included in an amount of less than 5% (wt/wt of the total formulation), such as about 4%, about 3%, about 2%, about 1% or less than about 1%.

The surfactant can be added either at the solid dispersion or tabletting stage.

Tabletting Process

In certain embodiments the pre-tabletting formulation excipients and solid-dispersion (including the compound of formula (I) may be combined and advantageously processed via a dry granulation process which may consist of intragranular blending, roller compaction, de-lumping and extragranular blending. This has been found to be advantageous as it further aids in maintaining the compound of formula (I) in the amorphous state. Furthermore, such a process has been found to produce granules of flow properties suitable for compression on a tablet press. The granules may be compressed at compression pressure ranging from 80-200 MPa.

Accordingly, in another aspect the invention provides for a method of preparing a pre-tabletting pharmaceutical composition comprising the steps of:

(i) preparing a solid dispersion comprising a compound of formula (I) in a substantially amorphous form:

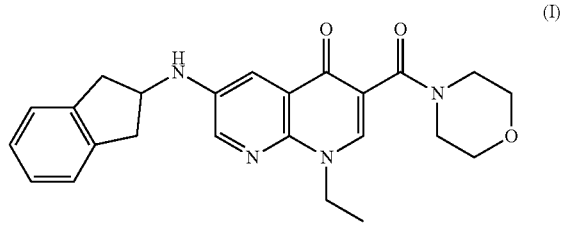 [SMILES: CCn1cc(C(=O)N2CCOCC2)c(=O)c2cc(NC3Cc4ccccc4C3)cnc21]

(I)

or a salt, or prodrug thereof;
by dispersing said compound of formula (I) within a polymer matrix formed by at least one pharmaceutically acceptable polymer;
(ii) mixing said solid dispersion from step (i) with at least one pharmaceutically acceptable excipient;
(iii) subjecting the resultant mixture from step (ii) to dry granulation; and
(iv) tabletting the dry granulation mixture of step (iii) by compression.

Treatment Methods

The present disclosure also contemplates the treatment or prophylaxis of a disease of the central nervous system, such as mood disorders (e.g., depression), anxiety disorders, and neurodegenerative diseases. The term neurodegenerative disease encompasses a condition leading to the progressive loss of structure or function of neurons, including death of neurons. Examples of neurodegenerative diseases contemplated herein include AIDS dementia complex, adrenoleukodystrophy, alexander disease, Alpers' disease, amyotrophic lateral sclerosis, ataxia telangiectasia, Batten disease, bovine spongiform encephalopathy, brainstem and cerebellum atrophy, Canavan disease, corticobasal degeneration, Creutzfeldt-Jakob disease, dementia with Lewy bodies, fatal familial insomnia, Friedrich's ataxia, familial spastic paraparesis, frontotemporal lobar degeneration, Huntington's disease, infantile Refsum disease, Kennedy's disease, Krabbe disease, Lyme disease, Machado-Joseph disease, monomelic amyotrophy, multiple sclerosis, multiple system atrophy, neuroacanthocytosis, Niemann-Pick disease, neurodegeneration with brain iron accumulation, opsoclonus myoclonus, Parkinson's disease, Pick's disease, primary lateral sclerosis, progranulin, progressive multifocal leukoencephalopathy, progressive supranuclear palsy, protein aggregation, Refsum disease, Sandhoff disease, diffuse myelinoclastic sclerosis, Shy-Drager syndrome, spinocerebellar ataxia, spinal muscular atrophy, spinal and bulbar muscular atrophy, subacute combined degeneration of spinal cord, Tabes dorsalis, Tay-Sachs disease, toxic encephalopathy, transmissible spongiform encephalopathy, and Wobbly hedgehog syndrome.

In certain embodiments, the tablet comprising compound (I), can be used to treat, ameliorate the signs and/or symptoms of, prevent, or otherwise delay the onset or development of the CNS disease, disorder, or condition.

Taught herein, therefore, is the use of a tablet formulation comprising compound (I), in the manufacture of a medicament for treating and/or preventing central nervous system disorders, such as mood disorders (e.g., depression), anxiety disorders, or neurodegenerative diseases, in a subject in need thereof.

Also provided herein are methods of treating and/or preventing central nervous system disorders, such as mood disorders (e.g., depression), anxiety disorders, or neurodegenerative diseases comprising the administration of an effective amount of a tablet comprising compound (I), to a subject in need thereof.

As used herein mood disorders are broadly recognized and clearly defined by the relevant DSM-IV-TR (Diagnostic and Statistical Manual of Mental Disorders, 4th Edition, Text Revision) criteria. Thus, there are depressive disorders of which the best known and most researched is major depressive disorder (MDD) commonly called clinical depression or major depression, and bipolar disorder (BD), formerly known as manic depression and characterized by intermittent episodes of mania or hypomania, usually interlaced with depressive episodes. Other depressive disorders include: atypical depression, melancholic depression, psychotic major depression, catatonic depression, postpartum depression, seasonal affective disorder, dysthymia, depressive disorder not otherwise specified (DD-NOS) (e.g., recurrent brief depression, minor depressive disorder), substance induced mood disorders (e.g., alcohol induced mood disorders, benzodiazepine induced mood disorders, interferon-alpha induced mood disorders).

Persons of skill in the art will be familiar with the lag period of traditional antidepressant medications, and with the heightened anxiety produced by the newer generation antidepressants, including SSRI's, SNRI's and NRI's in the early stages of treatment before the antidepressant effects are seen (within 2-4 weeks). Thus, in certain embodiments, the compounds described herein can be administered to a subject in need thereof as a substitute or replacement for traditional antidepressant medication. In other embodiments, compounds described herein can be administered to a subject in need thereof as a supplement to traditional antidepressant medication. In other embodiments, there is provided a method for treating or preventing depression in a subject, the method including the step of administering to said subject a tablet described herein, in the absence of adjunct antidepressant therapy.

Replacing traditional antidepressant medication with the present tablet can be advantageous, particularly where the traditional medication is associated with one or more adverse effects (e.g., anxiety, nausea, headaches, erectile dysfunction, early-onset suicidal tendencies, etc.). Examples of traditional antidepressant medication would be known to those skilled in the art and include, but are not limited to, selective serotonin re-uptake inhibitors (SSRI), serotonin/noradrenalin re-uptake inhibitors, selective noradrenalin re-uptake inhibitors, monoamine oxidase inhibitors, tricyclic antidepressants, lithium and other mood stabilisers, atypical antidepressants, and hormones such as estrogen or progestogen.

In other embodiments, the present tablet can be administered to a subject in need thereof, together with traditional antidepressants for a period of about 2-4 weeks, to address the symptoms of depression, with the option of discontinuing treatment with the present compounds whilst continuing with the traditional therapy. In other embodiments, the subject is treated with both a present tablet and one or more traditional antidepressant medications (administered sequentially or in combination) for the duration of the treatment period. Such combination therapy may be particularly useful, for example, where the combination of the present tablet formulation and one or more traditional antidepressant medications provides relief from depression in the acute lag phase of the treatment period and/or where an additive or synergistic antidepressant therapeutic effect is desired.

Depression relapse can also occur in patients treated with traditional antidepressant medication. Many such compounds are administered for anywhere from months to years and a reduction in efficacy is often seen with such long-term use, leading to significant continuing depression and dysfunction. Depression relapse may be sudden onset for some patients, while for others it might be evident as a gradual decline in mood and function, which diminishes over time as the patient approaches the state of relapse. Thus, patients who experience sudden onset of depression relapse or a gradual depression relapse would benefit from the methods disclosed herein, as the present tablet formulation can offset the diminishing effect of traditional antidepressant therapy. Thus, the use of the present tablet formulation may prevent or partly alleviate depression relapse often seen in patients taking traditional antidepressant medication.

Thus, in certain embodiments, provided herein are methods for treating or preventing relapse in a subject receiving antidepressant therapy, the method including the step of administering to said subject a tablet described herein comprising compound (I).

The traditional antidepressant therapies that are associated with potential depression relapse in a subject would be known to those skilled in the art. Examples include, but are not limited to, dosage increases, alternative SSRIs or SNRIs, and non-SSRI antidepressants such as noradrenaline re-uptake inhibitors, monoamine oxidase inhibitors, tricyclic antidepressants, lithium and other mood stabilisers, atypical antidepressants and hormones such as estrogen and progestogen, also referred to herein as "second antidepressant compounds."

The desired therapeutic activity, or effect, will typically depend on the condition being treated. For example, where the subject is being treated for depression, the therapeutic effect may be a reduction in at least one clinical symptom of depression, including, but not limited to, cognitive impairment, loss of appetite, mood, and/or inactivity.

In certain embodiments, the tablet formulation described herein, is administered to said subject sequentially (i.e., before or after) or in combination with a second antidepressant compound (e.g., with existing antidepressant therapy).

In certain embodiments, the tablet formulation disclosed herein has the further added advantage over traditional therapy in that it exhibits reduced sedative side effects which may adversely affect a subject's quality of life. In certain embodiments, the tablet formulation disclosed herein is free of measurable sedative side effects.

Sudden discontinuation of antidepressant medication may produce withdrawal effects caused by physical dependence on the drug. Compounds can be evaluated for physical dependence in a simple animal model where, following a period of chronic dosing (e.g., for 14-20 days), the study drug is stopped and measurements of food intake, body weight and body temperature are taken over the next 5 days. The symptoms of abrupt discontinuation of the drug are manifest as significantly reduced appetite, weight loss, and drop in body temperature. This model is suitable for detecting the effects across a broad range of drug classes including opiates, antidepressants, and benzodiazepines. The compound, or pharmaceutical compositions thereof described herein also can be used as a combination therapy, e.g., combining the treatment with other antidepressants such as benzodiazepines (e.g., alprazolam, diazepam, lorazepam, clonezepam), selective serotonin re-uptake inhibitors (SSRI) (e.g., citalopram, dapoxetine, escitalopram, fluoxetine, fluvoxamine, indalpine, paroxetine, sertraline, zimelidine, vilaxodone), serotonin norepinephrine reuptake inhibitors (SNRI) (e.g., venlafaxine, duloxetine, desvenlafaxine, milnacipran), monoamine oxidase inhibitors (e.g., phenelzine, moclobemide), tricyclic antidepressants (e.g., trimipramine, imipramine), tetracyclic antidepressants (e.g., mertazepine, maprotiline), mood stabilisers (e.g. lithium, sodium valproate, valproic acid), atypical antidepressants (e.g., bupropion), acetylcholinesterase inhibitors (e.g., donepezil, galantamine, rivastigmine), atypical antipsychotics (e.g., risperidone, aripiprizole, quetiapine, olanzapine), and hormones such as estrogen and progestogen.

It will thus be understood that the tablet formulations described herein, can be used in the treatment and/or prevention of any disease state, disorder, or condition which may be ameliorated by enhancement of neurite outgrowth.

In certain embodiments, the neurite outgrowth-responsive disease is a neurodegenerative disease. In a certain embodiments, the neurodegenerative disease is multiple sclerosis or a Parkinsonian related disorder. In a further embodiment, the neurodegenerative disease is multiple sclerosis. In a further embodiment the disease may involve a condition which involves neural damage including wound healing, spinal cord injury, peripheral nerve disorders.

Also contemplated herein is a sub-threshold disease, condition, state, disorder or trauma. In an embodiment, the disease, condition, state, disorder, or trauma is defined by its symptoms. Hence, the tablet formulations described herein may be useful in ameliorating the symptoms of a disease, condition, state, disorder, or trauma of the CNS. By "trauma" this includes stroke, brain haemorrhage, or another condition or event of the systemic vasculature which affects the CNS. The symptoms of a disease, condition, state, disorder, or trauma of the CNS would be familiar to those skilled in the art. Examples of such symptoms include mood disorders, such as depression. Thus, in certain embodiments, the tablet formulations described herein are used in the treatment of depression attributed to (or associated with) a neurodegenerative disease in the subject.

The tablet formulations described herein may also be used as therapy, e.g., combining the treatment with other neurodegenerative treatments, such as acetylcholineesterase inhibitors (e.g., Aricept, Exelon), and treatments for multiple sclerosis (e.g., Avonex, Betaseron, Copaxone, Tysabri, Gilenya).

It will be understood that tablet formulations described herein, can be used in the treatment of anxiety or conditions/disease states associated with anxiety such as irritable bowel syndrome and fibromyalgia.

In certain embodiments, an anxiety disorder is classified as one of the following:
 panic disorder,
 anxiety associated with autism,
 obsessive-compulsive disorder (OCD),
 post-traumatic stress disorder (PTSD),
 social phobia (or social anxiety disorder—(SAD)),
 specific phobias,
 generalized anxiety disorder (GAD),
 substance-induced anxiety disorder, and
 acute stress disorder (ASD).

In certain embodiments, the tablet formulations, as described herein may be used in the treatment of a panic disorder.

In certain embodiments, the tablet formulations, as described herein may be used in the treatment of autism.

In certain embodiments, the tablet formulations, as described herein may be used in the treatment of obsessive-compulsive disorder (OCD).

In certain embodiments, the tablet formulations, as described herein may be used in the treatment of agitation in, for instance, the elderly.

In certain embodiments, the tablet formulations, as described herein may be used in the treatment of post-traumatic stress disorder (PTSD).

In an embodiment the tablet formulations, as described herein may be used in the treatment of social phobia (or social anxiety disorder—SAD).

In certain embodiments, the tablet formulations, as described herein may be used in the treatment of specific phobias.

In certain embodiments, the tablet formulations, as described herein may be used for agoraphobia or agoraphobia without history of panic disorder.

In certain embodiments, the tablet formulations, as described herein may be used for animal phobia.

In certain embodiments, the tablet formulations, as described herein may be used in the treatment of substance-induced anxiety disorder.

In certain embodiments, the tablet formulations, as described herein may be used in the treatment of acute stress disorder (ASD).

In certain embodiments, the tablet formulations, as described herein may be used in the treatment of generalized anxiety disorder (GAD).

Generalised anxiety disorder criteria include:
(i) At least 6 months of "excessive anxiety and worry" about a variety of events and situations. Generally, "excessive" can be interpreted as more than would be expected for a particular situation or event. Most people become anxious over certain things, but the intensity of the anxiety typically corresponds to the situation.
(ii) There is significant difficulty in controlling the anxiety and worry. If someone has a very difficult struggle to regain control, relax, or cope with the anxiety and worry, then this requirement is met.
(iii) The presence for most days over the previous six months of 3 or more (only 1 for children) of the following symptoms:
 1. Feeling wound-up, tense, or restless
 2. Easily becoming fatigued or worn-out
 3. Concentration problems
 4. Irritability
 5. Significant tension in muscles
 6. Difficulty with sleep
(iv) The symptoms are not part of another mental disorder.
(v) The symptoms cause "clinically significant distress" or problems functioning in daily life. "Clinically significant" is the part that relies on the perspective of the treatment provider. Some people can have many of the aforementioned symptoms and cope with them well enough to maintain a high level of functioning.
(vi) The condition is not due to a substance or medical issue.

In certain embodiments, the tablet formulations, as described herein may be identified by one or more of the above criteria for generalized anxiety disorder.

In certain embodiments, the tablet formulations, as described herein may be used to treat or prevent one or more symptoms associated with an anxiety disorder.

Each anxiety disorder has different symptoms, but all the symptoms cluster around excessive, irrational fear and dread.

In another embodiment the tablet formulations, as described herein may be used in the treatment of depression, for instance, major depressive disorder.

Major depressive disorder criteria include:
(i) At least five of the following symptoms have been present during the same 2-week period and represent a change from previous functioning: at least one of the symptoms is either
 1) depressed mood or
 2) loss of interest or pleasure.
(ii) Depressed mood most of the day, nearly every day, as indicated either by subjective report (e.g., feels sad or empty) or observation made by others (e.g., appears tearful).

(iii) Markedly diminished interest or pleasure in all, or almost all, activities most of the day, nearly every day (as indicated either by subjective account or observation made by others).
(iv) Significant weight loss when not dieting or weight gain (e.g., a change of more than 5% of body weight in a month), or decrease or increase in appetite nearly every day.
(v) Insomnia or hypersomnia nearly every day.
(vi) Psychomotor agitation or retardation nearly every day (observable by others, not merely subjective feelings of restlessness or being slowed down).
(vii) Fatigue or loss of energy nearly every day.
(viii) Feelings of worthlessness or excessive or inappropriate guilt (which may be delusional) nearly every day (not merely self-reproach or guilt about being sick).
(ix) Diminished ability to think or concentrate, or indecisiveness, nearly every day (either by subjective account or as observed by others).
(x) Recurrent thoughts of death (not just fear of dying), recurrent suicidal ideation without a specific plan, or a suicide attempt or specific plan for committing suicide.
(xi) The symptoms do not meet criteria for a mixed episode.
(xii) The symptoms cause clinically significant distress or impairment in social, occupational, or other important areas of functioning.
(xiii) The symptoms are not due to the direct physiological effects of a substance (e.g. a drug of abuse, a medication) or a general medical condition (e.g., hypothyroidism).
(xiv) The symptoms are not better accounted for by bereavement, i.e., after the loss of a loved one, the symptoms persist for longer than 2 months or are characterized by marked functional impairment, morbid preoccupation with worthlessness, suicidal ideation, psychotic symptoms, or psychomotor retardation.

The above criteria have been sourced from the American Psychiatric Association (2000) Diagnostic and Statistical Manual of Mental Disorders (4th Ed., Text Revision). Washington D.C.: American Psychiatric Association.

In certain embodiments, the tablet formulations, as described herein may be identified by one or more of the above criteria for major depressive disorder.

In another embodiment the tablet formulations, as described herein may be used to treat or prevent one or more symptoms associated with depression.

Further disorders for which the tablet formulations, as described herein may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic subjects; hearing disorders, including tinnitus and age-related hearing impairment; urinary incontinence; and the effects of substance abuse or dependency, including alcohol withdrawal, neuroses, convulsions, migraine, depressive disorder, bipolar disorder, psychotic disorder, neurodegeneration arising from cerebral ischemia, attention deficit hyperactivity disorder, Tourette's syndrome, speech disorder, disorders of circadian rhythm, single-episode or recurrent major depressive disorder, dysthymic disorder, bipolar I or bipolar II manic disorder, cyclothymic disorder, schizophrenia, and stuttering.

In an embodiment the tablet formulations, as described herein may be used in the treatment of cerebral ischemia. In certain embodiments, the tablet formulations, as described herein may be used in the treatment of neurodegeneration arising from cerebral ischemia.

In an embodiment the tablet formulations, as described herein may be used in the treatment of disorders of the circadian rhythm.

In an embodiment the tablet formulations, as described herein may be used in the treatment of pain and nociception.

In an embodiment the tablet formulations, as described herein may be used in the treatment of Alzheimer's disease.

It should be appreciated that the tablet formulations, a described herein can be administered to a subject in a treatment effective amount. In some embodiments, a treatment effective amount is a therapeutically effective amount or a prophylactically effective amount. The term "therapeutically effective amount" as used herein means that amount of active compound or pharmaceutical agent that elicits the biological or medicinal response in a tissue, system, animal or human that is being sought by a researcher, veterinarian, medical doctor, or other clinician. The therapeutically effective amount of the compound to be administered will be governed by such considerations, and is the minimum amount necessary to ameliorate, cure, or treat the disease or disorder or one or more of its symptoms. The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease or symptom) and secondary prophylaxis (whereby the disease or symptom has already developed and the subject is protected against worsening of this process).

As used herein, the term "effective amount" relates to an amount of a tablet formulation, which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 1 g per kg of body weight per dosage. The dosage may be in the range of 1 µg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

In certain embodiments, a provided method comprises administering to a subject in need thereof the present tablet formulations, in a dosage to provide an effective amount in vivo that will enhance neurite outgrowth (neurogenesis), including, but not limited to the acute stages of treatment (e.g., within 1, 2, 3, or 4 weeks from the commencement of treatment). In an embodiment, an effective amount in vivo has an in vitro equivalent concentration that is sufficient to increase neurite outgrowth by at least 5%, at least 10%, at least 20%, or at least 50% in a neurite outgrowth assay, for example, a neurite outgrowth assay described herein. Methods of determining an in vitro equivalent concentration of the present compounds would be familiar to the skilled artisan. For example, at from about 10 minutes to about 60 minutes after administration of the present compounds to a subject, a blood sample is taken and assayed by HPLC, ELISA, gas chromatography, or by other suitable assay to determine the concentration per ml of blood. An equivalent effective concentration can then be used in an in vitro assay once factors such as the weight of the subject, the appropriate blood volume of the subject and the appropriate rate of diffusion of the present compound across the blood-brain barrier are taken into account. In another embodiment, when the present tablet formulations is found to stimulate neurite outgrowth in vitro (as compared to a control), an approximate in vivo effective amount can be determined for a subject by extrapolating the in vitro concentration to an in vivo equivalent. Factors such as the weight of the subject, the appropriate blood volume of the subject and the appropriate rate of diffusion of the present compound across the blood-brain barrier may be used to extrapolate an in vivo effective amount and hence the appropriate dosage amount that would give rise to said in vivo effective amount.

Thereafter, treatment with the tablet formulations, may be continued throughout the treatment period or it may be ceased or replaced with traditional therapeutic compounds. Methods of determining the effective amount of the tablet formulations, that is required for enhancing neurite outgrowth (neurogenesis) in vivo would be familiar to those skilled in the art. For example, enhancement of neurogenesis can be determined by measuring a symptom of the CNS disorder including, but not limited to, cognitive impairment, degree and frequency of seizures or tremors, motordysfunction, headaches and mood (e.g., degree of happiness).

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

In certain embodiments, an effective amount of the tablet formulations for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the tablet formulations may be at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect.

Suitable dosage amounts and dosing regimens can be determined by the attending physician and may depend on the particular condition being treated, the severity of the condition as well as the general age, health and weight of the subject. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The tablet formulation described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another anti-anxiety or anti-depressant medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed.

When "combination therapy" is employed, an effective amount can be achieved using a first amount of the tablet formulations, and a second amount of an additional suitable therapeutic agent.

In certain embodiments, the tablet formulations as described herein, and the additional therapeutic agent are each administered in an effective amount (i.e., each in an amount which would be therapeutically effective if administered alone). In other embodiments, the tablet formulations as described herein, and the additional therapeutic agent are each administered in an amount which alone does not provide a therapeutic effect (a sub-therapeutic dose). In yet other embodiments, the tablet formulations as described herein can be administered in an effective amount, while the additional therapeutic agent is administered in a sub-therapeutic dose. In still other embodiments, the tablet formulations as described herein, can be administered in a sub-therapeutic dose, while the additional therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, tablet having a fixed ratio of first and second amounts, or in multiple, separate tablets for each. In addition, such co-administration also encompasses use of each compound in a sequential manner in either order. When co-administration involves the separate administration of the first amount of the tablet formulations as described herein, and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life, and kinetic profile. For example, the tablet formulations as described herein, and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Examples of therapeutic agents that may be combined with the tablet formulations, either administered separately or in the same pharmaceutical composition, include, but are not limited to, muscle relaxants, anticonvulsants, hypnotics, anesthetics, analgesics, cholinergics, antidepressants, mood stabilisers, and anxiolytics.

In certain embodiments, a second therapeutic agent is a SSRI selected from the following: citalopram (Celexa, Cipramil, Cipram, Dalsan, Recital, Emocal, Sepram, Seropram, Citox, Cital), dapoxetine (Priligy), escitalopram (Lexapro, Cipralex, Seroplex, Esertia), fluoxetine (Prozac, Fontex, Seromex, Seronil, Sarafem, Ladose, Motivest, Flutop, Fluctin (EUR), Fluox (NZ), Depress (UZB), Lovan (AUS), Prodep (IND)), fluvoxamine (Luvox, Fevarin, Faverin, Dumyrox, Favoxil, Movox), paroxetine (Paxil, Seroxat, Sereupin, Aropax, Deroxat, Divarius, Rexetin, Xetanor, Paroxat, Loxamine, Deparoc), sertraline (Zoloft, Lustral, Serlain, Asentra), and vilazodone (Viibryd).

In certain embodiments, a second therapeutic agent is a tetracyclic antidepressant (TeCA) selected from the group consisting of: amoxapine (Amokisan, Asendin, Asendis, Defanyl, Demolox, Moxadil), maprotiline (Deprilept, Ludiomil, Psymion), mazindol (Mazanor, Sanorex), mianserin (Bolvidon, Depnon, Norval, Tolvon), mirtazapine (Remeron, Avanza, Zispin, Miro), and setiptiline (Tecipul).

In certain embodiments, a second therapeutic agent is a serotonin-noradrenaline reuptake inhibitor (SNRI) selected from the group consisting of: desvenlafaxine (Pristiq), duloxetine (Cymbalta, Ariclaim, Xeristar, Yentreve, Duzela), milnacipran (Ixel, Savella, Dalcipran, Toledomin), and venlafaxine (Effexor, Efexor).

In certain embodiments, a second therapeutic agent is a Noradrenaline reuptake inhibitor (NRI) selected from the group consisting of: atomoxetine (Tomoxetine, Strattera, Attentin), mazindol (Mazanor, Sanorex), reboxetine (Edronax, Norebox, Prolift, Solvex, Davedax, Vestra), and viloxazine (Vivalan, Emovit, Vivarint, Vicilan).

In certain embodiments, a second therapeutic agent is a monoamine oxidase inhibitor (MAOI) selected from the group consisting of: benmoxin (Nerusil, Neuralex), hydralazine (Apresoline), iproclozide (Sursum), iproniazid (Marsilid, Iprozid, Ipronid, Rivivol, Propilniazida), isocarboxazid (Marplan), isoniazid (Laniazid, Nydrazid), mebanazine (Actomol), nialamide (Niamid), octamoxin (Ximaol, Nimaol), phenelzine (Nardil, Nardelzine), pheniprazine (Catron), phenoxypropazine (Drazine), pivalylbenzhydrazine (Tersavid), procarbazine (Matulane, Natulan, Indicarb), caroxazone (Surodil, Timostenil), echinopsidine (Adepren), furazolidone (Furoxone, Dependal-M), linezolid (Zyvox, Zyvoxam, Zyvoxid), tranylcypromine (Parnate, Jatrosom), brofaromine (Consonar), metralindole (Inkazan), minaprine (Cantor), moclobemide (Aurorix, Manerix), pirlindole (Pirazidol), toloxatone (Humoryl), lazabemide (Pakio, Tempium), pargyline (Eutonyl), rasagiline (Azilect), and selegiline (Deprenyl, Eldepryl, Emsam).

In certain embodiments, a second therapeutic agent is a tricyclic antidepressant (TCA) selected from the group consisting of: amitriptyline (Tryptomer, Elavil, Tryptizol, Laroxyl, Sarotex, Lentizol), butriptyline (Evadene, Evadyne, Evasidol, Centrolese), clomipramine (Anafranil), desipramine (Norpramin, Pertofrane), dosulepin (Prothiaden, Dothep, Thaden and Dopress), doxepin (Aponal, Adapine, Doxal, Deptran, Sinquan, Sinequan, Zonalon, Xepin, Silenor), imipramine (Antideprin, Deprimin, Deprinol, Depsol, Depsonil, Dynaprin, Eupramin, Imipramil, Irmin, Janimine, Melipramin, Surplix, Tofranil), lofepramine (Gamanil, Tymelyt, Lomont), nortriptyline (Sensoval, Aventyl, Pamelor, Norpress, Allegron, Noritren, Nortrilen), Protriptyline (Vivactil), and trimipramine (Surmontil, Rhotrimine, Stangyl).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Throughout this specification and the claims which follow, unless the context requires otherwise, the phrase "consisting essentially of", and variations such as "consists essentially of" will be understood to indicate that the recited element(s) is/are essential i.e. necessary elements of the invention. The phrase allows for the presence of other non-recited elements which do not materially affect the characteristics of the invention but excludes additional unspecified elements which would affect the basic and novel characteristics of the method defined.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

Further features of the present invention are more fully described in the following non-limiting examples.

EXAMPLES

Example 1 (Ex1): Preparation of Representative Spray Dried Dispersion (SDD) Compositions of Invention Approximately 150 g of compound (I), also known as "BNC210", was dissolved in 4 kg of a mixture of dichloromethane and methanol (80:20% w/w). The appropriate amount of a polymer (Table 1) was added to the solution and the mixture was stirred leading to a homogeneous solution. Alternatively, additional excipients, such as SLS sodium laurel sulfate, were added. The solution was spray dried using Büchi B290 spray dryer with 2-fluid nozzle. The representative composition of the spray dried dispersion powders and their physical appearance are given in Table 1.

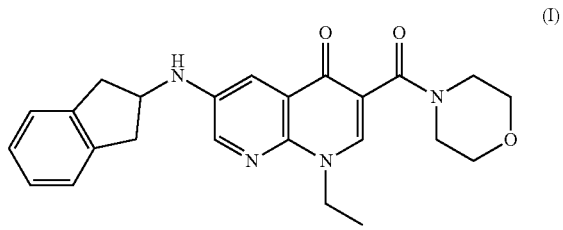 [SMILES: CCn1cc(C(=O)N2CCOCC2)c(=O)c2cc(NC3Cc4ccccc4C3)cnc21]

Example 2 (Ex2): Preparation of Representative Hot Melt Extrusion (HME) Dispersion Compositions of Invention Approximately 6 g of compound (I), also known as "BNC210", and HPMCAS-H polymer were blended using Turbula Blender, de-lumped the blend through 25 mesh and blended again. The blended mixture was fed into HAAKE Mini CTW Extruder at 165 or 175 or 180° C. with counter screw rotating configuration at a screw speed of 200 rpm and pressed through a die. Optionally the rolls were chilled with dry ice to quench cool the extrudate. The extrudate was milled though size 60 mesh screen.

The representative composition of the hot melt extrusion extrudate and their physical appearance are given in Table 2.

TABLE 1

Representative composition of the spray dried dispersion powders and their physical appearance.

| | Formulation | | | | |
|---|---|---|---|---|---|
| | 30:70 BNC210: HPMCAS-H | 40:60 BNC210: HPMCAS-H | 50:50 BNC210: HPMCAS-H | 60:40 BNC210: HPMCAS-H | 70:30 BNC210: HPMCAS-H |
| SDD Lot Number | B12-705-35 | B12-705-36 | B12-705-37 | B12-705-38 | B12-705-39 |
| Spray Solvent | 80:20 DCM:MeOH | 80:20 DCM:MeOH | 80:20 DCM:MeOH | 80:20 DCM:MeOH | 80:20 DCM:MeOH |
| Spray Solution (wt % total solids) | 7.9 | 7.0 | 6.0 | 5.0 | 4.0 |
| Dry SDD Yield (%) | 73.9 | 80.9 | 77.6 | 56.6 | 62.9 |
| Physical Appearance | Yellow Powder | Yellow Powder | Yellow Powder | Yellow Powder | Yellow Powder |

| | Formulation | | | | |
|---|---|---|---|---|---|
| | 30:70 BNC210: HPMC E15 LV | 40:60 BNC210: HPMC E15 LV | 50:50 BNC210: HPMC E15 LV | 60:40 BNC210: HPMC E15 LV | 70:30 BNC210: HPMC E15 LV |
| SDD Lot Number | B12-705-40 | B12-705-41 | B12-705-42 | B12-705-43 | B12-705-44 |
| Spray Solvent | 80:20 DCM:MeOH | 80:20 DCM:MeOH | 80:20 DCM:MeOH | 80:20 DCM:MeOH | 80:20 DCM:MeOH |
| Spray Solution (wt % total solids) | 4.9 | 4.2 | 6.0 | 5.0 | 4.0 |
| Dry SDD Yield (%) | 72.0 | 81.7 | 80.2 | 81.8 | 90.7 |

| | Formulation | | | | |
|---|---|---|---|---|---|
| | 30:70 BNC210: HPMCAS-M | 50:50 BNC210: HPMCAS-M | 30:70 BNC210: CAP | 50:50 BNC210: CAP | 30:70 BNC210: Eudragit L100 |
| SDD Lot Number | B12-705-71 | B12-705-72 | B12-705-73 | B12-705-74 | B12-705-75 |
| Spray Solvent | 80:20 DCM:MeOH | 80:20 DCM:MeOH | 80:20 DCM:MeOH | 80:20 DCM:MeOH | 80:20 DCM:MeOH |
| Spray Solution (wt % total solids) | 8.0 | 6.0 | 8.0 | 6.0 | 8.0 |

TABLE 1-continued

Representative composition of the spray dried dispersion powders and their physical appearance.

| Dry SDD Yield (%) | 71.2 Yellow Powder | 99.6 Yellow Powder | 85.9 Yellow Powder | 90.2 Yellow Powder | 40.0 Fluffy Yellow Powder |
|---|---|---|---|---|---|

| | Formulation | | | | |
|---|---|---|---|---|---|
| | 50:50 BNC210: Eudragit L100 | 30:70 BNC210: HPMCAS-L | 30:70 BNC210: PVP-VA | 100% BNC210 | |
| SDD Lot Number | B12-705-76 | B12-705-6 | B12-705-9 | B12-705-77 | |
| Spray Solvent | 80:20 DCM:MeOH | 80:20 DCM:MeOH | 80:20 DCM:MeOH | 80:20 DCM:MeOH | |
| Spray Solution (wt % total solids) | 6.0 | 10 | 10 | 3.0 | |
| Dry SDD Yield (%) | 71.2 | 86 | 86 | 74.0 | |
| Physical Appearance | Yellow Powder | Yellow Powder | Yellow Powder | Yellow Powder | |

TABLE 2

Representative composition of hot melt extrusion extrudate and physical appearance.

| | Formulation | | | | |
|---|---|---|---|---|---|
| | 40:60 BNC210: HPMCAS-H | 55:45 BNC210: HPMCAS-H | 40:60 BNC210: HPMCAS-M | 55:45 BNC210: HPMCAS-M | 40:60 BNC210:HPMC E15 LV |
| HME Lot Number | B12-705-78-1-A | B12-705-78-1-B | B12-705-78-2-A | B12-705-78-2-B | B12-705-78-3-A |
| Chamber temperature (° C.) | 180 | 180 | 180 | 180 | 180 |
| Physical Appearance Of extrudate | Translucent yellow brittle | Translucent yellow/brown brittle | Translucent yellow brittle | Translucent Brown brittle | Opaque tan, rough exterior, brittle |
| Cool Quench | No | No | No | No | No |

| | Formulation | | |
|---|---|---|---|
| | 40:60 BNC210: HPMCAS-H | 55:45 BNC210: HPMCAS-H | 55:45 BNC210: HPMCAS-H |
| HME Lot Number | B12-705-81 | B12-705-82 | B12-705-83 |
| Chamber temperature (° C.) | 180 | 180 | 180 |
| Physical Appearance Of extrudate | Translucent yellow brittle | Translucent brown brittle | Clear extrudate initially, then opaque |
| Cool Quench | Yes | No | Yes |

Determination of Thermal Properties and Crystallinity

Modulated differential scanning calorimetry (mDSC) was used to characterize the compositions of the invention (both spray dried and HME based compositions). Solid samples were placed in hermetically sealed aluminum pan with a pinhole. Modulation amplitude off ±1.0° C. with a period of 60 sec was applied to the sample heated at 2° C./min under dried nitrogen purge using TA instruments (New Castle, Del., USA) model Q2000 with RCS90 chiller. The compositions of the inventions display single glass transition ($T_g$) temperature as given in Table 3 and shown in FIGS. 2a, 2b and 2c.

TABLE 3

Glass transition temperature ($T_g$) of Representative composition of the spray dried and hot melt extrusion dispersion powders

| Sample Description | Lot | Tg(° C.) |
|---|---|---|
| Spray Dried Dispersions | | |
| 30:70 BNC210:HPMCAS-H | B12-705-35 | 97 |
| 40:60 BNC210:HPMCAS-H | B12-705-36 | 95 |
| 50:50 BNC210:HPMCAS-H | B12-705-37 | 95 |
| 60:40 BNC210:HPMCAS-H | B12-705-38 | 96 |
| 70:30 BNC210:HPMCAS-H | B12-705-39 | 96 |
| 30:70 BNC210:HPMC E15LV | B12-705-40 | 109 |
| 40:60 BNC210:HPMC E15LV | B12-705-41 | 106 |
| 50:50 BNC210:HPMC E15LV | B12-705-42 | 103 |
| 60:40 BNC210:HPMC E15LV | B12-705-43 | 102 |
| 70:30 BNC210:HPMC E15LV | B12-705-44 | 101 |
| 30:70 BNC210:HPMCAS-M | B12-705-71 | 98 |
| 50:50 BNC210:HPMCAS-M | B12-705-72 | 96 |
| 30:70 BNC210:CAP | B12-705-73 | 139 |
| 50:50 BNC210:CAP | B12-705-74 | 126 |
| 30:70 BNC210:Eudragit L100 | B12-705-75 | 170 |
| 50:50 BNC210:Eudragit | B12-705-76 | 152 |
| 100% BNC210 SD | B12-705-77 | 100 |
| Hot Melt Extrusion Dispersions | | |
| 40:60 BNC210:HPMCAS-HMP (180° C.) | B12-705-78-1-A-2 | 96 |
| 55:45 BNC210:HPMCAS-HMP (180° C.) | B12-705-78-1-B-3 | 95 |

TABLE 3-continued

Glass transition temperature ($T_g$) of Representative composition of the spray dried and hot melt extrusion dispersion powders

| Sample Description | Lot | Tg(° C.) |
|---|---|---|
| 40:60 BNC210:HPMCAS-MMP (180° C.) | B12-705-78-2-A-2 | 96 |
| 55:45 BNC210:HPMCAS-MMP (180° C.) | B12-705-78-2-B-3 | 96 |
| 40:60 BNC210:HPMC E15 LV (180° C.) | B12-705-78-3-A-1 | 100 |
| 30:70 BNC210:HPMCAS-L | B12-705-6 | 100 |
| 30:70BNC210:PVP-VA | B12-705-9 | 105 |

The crystallinity of spray dried and hot melt extrusion dispersion compositions of invention was determined by powder X-ray diffraction (PXRD) using Rigaku Miniflex 6G benchtop X-ray diffractometer. The recommended parameters for PXRD recordings are given in Table 4.

TABLE 4

XRPD Parameters

| Instrument: | Rigaku Miniflex 6G |
|---|---|
| Radiation Source: | Cu-Kα (1.5406 Å) |
| Scan Mode: | Coupled 2θ/θ |
| Scan Range: | 5°-40° |
| Scan Speed: | 2°/min |
| Step Increment: | 0.005° |
| Voltage: | 40 kV |
| Current: | 15 mA |
| Rotation: | 30 rpm |
| Divergence Slit: | 0.625 mm |
| Knife Edge Width: | 1.0 mm |
| Sample Holder: | Zero-Background Cup |
| Method: | DM-0044 |

The spray dried and hot melt extrusion dispersion compositions of the invention show very broad peaks in XRPD (FIGS. 3a, 3b and 3c), indicating that these compositions are amorphous in nature.

Dissolution Testing

Compound I is a poorly soluble compound and exhibits moderate permeability, so its systemic absorption will be highly dependent on dissolution rate and precipitation from the small intestine. So, biorelevant dissolution testing experiments (solubility/precipitation) were carried out by suspending the dispersion powder in SGF (0.1N HCl, pH=1) medium, followed by transferring the solution to SIF (simulated intestine fluid: 2.24 mg/mL FaSSIF in 100 mM PBS). Appropriate amounts (equivalent to 2.0 mg/mL of compound I) of composition of invention were added to 50 mL of 0.1N HCl and stirred. The aliquots of mixture were withdrawn at 10 and 25 minutes, vortexed for 10 seconds and the dissolved amount was measure by analytical HPLC using external reference standards at a wavelength of 240 nm. After 30 minutes, the entire content of sample from SGF incubation was transferred into 50 mL of SIF media with stirring, and the dissolved amount was measured at 35, 50, 75, 120 and 210 minutes. A control experiment was performed using micronized powder of Compound I "as is" and the results are presented in Table 5 and FIGS. 4a, 4b, 4c, 4d and 4e. In SGF media, all spray dried compositions released higher amount of Compound I compared the micronized powder of Compound I "as is". HPMCAS-H and HPMC E15 LV polymer-based spray dried compositions released significantly higher amounts of Compound I in solution compared to HPMCAS-M, HPMCAS-M, CAP, Eudragit polymer-based compositions. The rapid increase in pH that occurred when the medium was changed from SGF to SIF, resulted in a sharp decrease in solubility of compound I and it precipitated out. Unpredictably, the amount of Compound I in solution for the HPMCAS-H, HPMCAS-M, HPMCAS-L and HPMC E15 LV based compositions did not decrease to the same extent as the PVP-VA, CAP and Eudragit polymer-based composition or Compound I "as is". In addition, the HPMCAS-H, HPMCAS-M and HPMC E15 LV based compositions exhibited a parachute effect whereby Compound I did not precipitate out as quickly, with the polymers assisting the compound to maintain solubility in the SIF media for longer.

TABLE 5

Dissolution testing of the dispersion compositions of invention

| Sample | Lot | Total Drug CmaxGB (µgA/mL) | Total Drug CmaxFaSSIF (µgA/mL) | Total Drug AUC 35-210 FaSSIF (min * µgA/mL) | Total Drug C210 (µgA/mL) | Increase in AUC over API AUC |
|---|---|---|---|---|---|---|
| 30:70 BNC210:HPMCAS-H | B12-705-35 | 767 | 627 | 50800 | 196 | 12 |
| 40:60 BNC210:HPMCAS-H | B12-705-36 | 675 | 554 | 52000 | 189 | 12 |
| 50:50 BNC210:HPMCAS-H | B12-705-37 | 522 | 386 | 55700 | 247 | 13 |
| 60:40 BNC210:HPMCAS-H | B12-705-38 | 637 | 321 | 50400 | 259 | 12 |
| 70:30 BNC210:HPMCAS-H | B12-705-39 | 454 | 293 | 49000 | 260 | 11 |
| 30:70 BNC210:HPMC E15LV | B12-705-40 | 606 | 323 | 43400 | 183 | 10 |
| 40:60 BNC210:HPMC E15LV | B12-705-41 | 540 | 283 | 47600 | 244 | 11 |
| 50:50 BNC210:HPMC E15LV | B12-705-42 | 743 | 385 | 45100 | 172 | 10 |
| 60:40 BNC210:HPMC E15LV | B12-705-43 | 860 | 430 | 46500 | 172 | 11 |
| 70:30 BNC210:HPMC E15LV | B12-705-44 | 638 | 328 | 52000 | 246 | 12 |
| 100% BNC210 SD | B12-705-77 | 158 | 68 | 8700 | 60 | 2 |
| BNC210 API | API | 88 | 32 | 4300 | 29 | NA |
| 30:70 BNC210:HPMCAS-M | B12-705-71 | 695 | 372 | 27800 | 125 | 6 |
| 50:50 BNC210:HPMCAS-M | B12-705-72 | 604 | 340 | 29700 | 133 | 7 |
| 30:70 BNC210:CAP | B12-705-73 | 170 | 457 | 16500 | 90 | 4 |
| 50:50 BNC210:CAP | B12-705-74 | 337 | 115 | 10500 | 69 | 2 |
| 30:70 BNC210:Eudragit L100 | B12-705-75 | 177 | 188 | 11800 | 74 | 3 |
| 50:50 BNC210:Eudragit L100 | B12-705-76 | 353 | 71 | 7700 | 51 | 2 |
| 30:70 BNC210:HPMCAS-L | B12-705-6 | 685 | 205.7 | 25500 | 118 | 4.3 |
| 30:70 BNC210:PVP-VA | B12-705-9 | 276 | 78.9 | 11900 | 65.5 | 2.0 |

Tablet Process

A demonstration batch of tablets (300 g blend, ~200 tablets) was manufactured by dry granulation using roller compactor, followed by tableting using rotary tablet press (B12-705-29). The dry granulation process consists of intragranular blending, roller compaction, de-lumping and extra granular blending, and produces granules of flow properties suitable for compression on the Riva Piccola rotary tablet press. The composition of intragranular and extragranular blend are given in the table 6.

TABLE 6

|  | ID | Component | Unit Composition (weight %) | mg/tablet |
|---|---|---|---|---|
| Intragranular | 1 | RUN #1: HPMCAS-M Spray Dried Dispersion (SDD) | 50.00 | 500.0 |
|  | 2 | Microcrystalline Cellulose (Avicel PH-105) | 41.25 | 412.5 |
|  | 3 | Croscarmellose Sodium (Ac-Di-Sol SD 711) | 1.00 | 10.0 |
|  | 4 | Colloidal Silica (Cab-O-Sil M-5P) | 1.00 | 10.0 |
|  | 5 | Sodium Stearyl Fumarate (Pruv SSF) | 0.50 | 5.0 |
|  |  | Intragranular Total | 93.75 | 937.5 |
| Extragranular | 7 | Microcrystalline Cellulose (Avicel PH-200) | 5.00 | 50.0 |
|  | 8 | Croscarmellose Sodium (Ac-Di-Sol SD 711) | 1.00 | 10.0 |
|  | 9 | Sodium Stearyl Fumarate (Pruv SSF) | 0.25 | 2.5 |
|  |  | Extragranular Total | 6.25 | 62.5 |
|  |  | Total | 100.00 | 1000.0 |

Step 1: Intragranular Blending
a) Weigh out desired amount of Avicel PH-105 and add into 5 L bin. Blend for 1 min at 20 rpm to coat the blender shell
b) Weigh out the desired amount of Run #1:HPMCAS-M SDD, Cab-O-Sil, Ac-Di-Sol, Pruv SSF and add into bin. Blend for 10 minutes at 20 rpm.
c) De-lump the blend by Comil (Quadro U5) using the settings as following
d) Screen=032R, Impeller=1612 and RPM=3000
e) Add de-lumped material back into bin and blend for 10 minutes at 20 rpm Step 2: Roller Compacting and Granulation
a) Charge Vector TFC-Lab Micro roller compactor with intragranular blend from step 1 and compacted to ribbon using roller compactor settings as: Roll speed=3.0 rpm, Screw Speed=50 rpm, and Roll pressure=10 MPa.
b) The ribbon was granulated with TFC Micro granulated using 18 mesh screen.

Step 3: Extra-Granular Blending & Granulation
a) The granulated blend from step 2 was added to 5.0 L bin and add appropriate amount of Avicel PH-200, Ac-Di-Sol and Pruv SSF (de-lump using 40 mesh prior to addition to the bin).
b) Blend the material for 10 minutes at 20 rpm and measure the physical parameters. Bulk/tapped density, Carr Index and Hausner Ratio of final blend is given in Table 7:

TABLE 7

| Bulk Density (g/cc) | Tapped Density (g/cc) | Carr Index | Hausner Ratio |
|---|---|---|---|
| 0.52 | 0.52 | 0.52 | 0.52 |

Step 4: Tableting
The granulated blend from step 3 was then compressed into tablets using Piva Piccola Rotary Tablet Press. The process parameters and the properties of resulting tablets are given in the Table 8.

TABLE 8

| Tooling: 0.4055" × 0.7480" Mod Oval | Tablet weight variation (n = 10): |
| Number of Stations: 1 | Average (mg): 1017, RSD %: 1.2 |
| Target Tablet weight: 1000 ± 50 mg | Tablet Thickness (n = 10): |
|  | Average (mm): 7.13, RSD % 1.0 |
|  | Tablet Breaking Force (n = 6): |
| Turret Speed: 20 rpm | Average (kPa): 31.6, RSD % 6.8 |
| Compression Pressure: 100 MPa (16.5 kN) | Friability (10 tablets): 0.03% |
| Pre-Compression: 150-280 N | Disintegration (n = 6): |
| Ejection Force: 340-385 N | First: 5 min 56 sec |
| Target Tablet Breaking Force: 30 ± 5 kPa | Last: 8 min 24 sec |
|  | Recommended weight working limit: 5% |
|  | Recommended weight alert limit: 7% |

The invention claimed is:
1. A solid dispersion comprising a compound of formula (I) or a salt, or prodrug thereof;

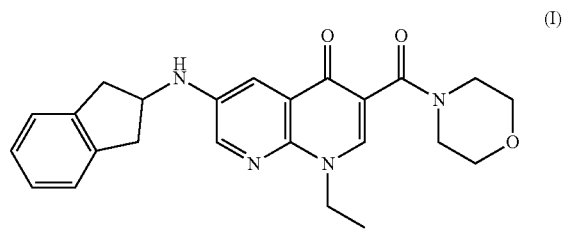 [SMILES: CCn1cc(C(=O)N2CCOCC2)c(=O)c2cc(NC3Cc4ccccc4C3)cnc21]

dispersed within a polymer matrix formed by at least one pharmaceutically acceptable polymer, optionally with one or more pharmaceutically acceptable surfactants, wherein the pharmaceutically acceptable polymer is a crystallization inhibitor polymer which is a hydroxypropyl methylcellulose acetate succinate (HPMCAS), and wherein the ratio of the compound of formula (I) or a salt thereof: crystallization inhibitor polymer is from 30:70 to 70:30 based on wt/wt % of the total solid dispersion, and wherein the solid dispersion comprises 50 mg-500 mg of the compound of formula (I) or salt thereof.

2. A tablet comprising a solid dispersion according to claim 1 together with one or more pharmaceutically acceptable excipients.

3. A tablet comprising:
(i) 50 mg-500 mg of a compound of formula (I) in substantially amorphous form:

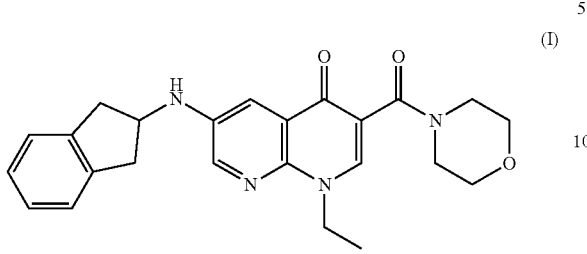

or a salt, or prodrug thereof; and
(ii) a crystallization inhibitor polymer;
wherein the ratio of (i):(ii) is from about 10:90 to about 80:20 (wt/wt %) %),
and wherein the crystallization inhibitor polymer is a hydroxypropyl methylcellulose acetate succinate (HPMCAS).

4. A solid dispersion formulation comprising:
(i) a compound of formula (I) in substantially amorphous form:

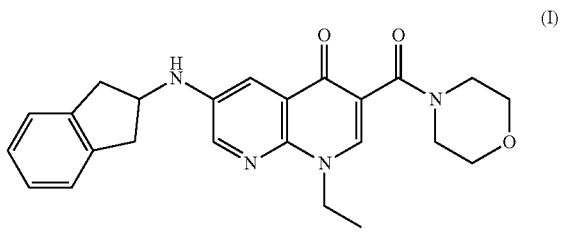 [SMILES: CCn1cc(C(=O)N2CCOCC2)c(=O)c2cc(NC3Cc4ccccc4C3)cnc21]

or a salt, or prodrug thereof; and
(ii) a crystallization inhibitor polymer;
wherein the ratio of (i):(ii) is from about 10:90 to about 80:20 (wt/wt %) %), and wherein the crystallization inhibitor polymer is a hydroxypropyl methylcellulose acetate succinate (HPMCAS).

5. A method of treating a disease of the central nervous system including the step of administering to a subject in need thereof an effective amount of a tablet comprising:
(i) 50 mg-500 mg of a compound of formula (I) in substantially amorphous form:

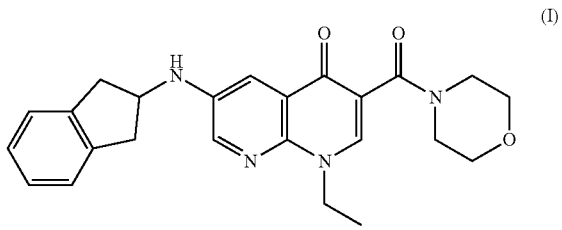 [SMILES: CCn1cc(C(=O)N2CCOCC2)c(=O)c2cc(NC3Cc4ccccc4C3)cnc21]

or a salt, or prodrug thereof; and
(ii) a crystallization inhibitor polymer;
wherein the ratio of (i):(ii) is from about 10:90 to about 80:20 (wt/wt %), and wherein the crystallization inhibitor polymer is a hydroxypropyl methylcellulose acetate succinate (HPMCAS).

6. The solid dispersion of claim 1, wherein the polymer or crystallization inhibitor polymer is HPMCAS selected from one of the various grades: L, M and H.

7. The solid dispersion of claim 6, wherein the polymer or crystallization inhibitor polymer is HPMCAS-H.

8. The solid dispersion of claim 6, wherein the polymer or crystallization inhibitor polymer is HPMCAS-M.

9. The solid dispersion of claim 1, with added surfactant such as which is selected from SLS or sorbates.

10. The solid dispersion of claim 1, wherein the weight ratio of compound of formula (I) to polymer ((i):(ii)) is from about 35:65, 40:60, 45:55, 50:50, 55:45 or about 60:40 (wt %/wt %).

11. The solid dispersion of claim 1 produced by spray drying.

12. The solid dispersion of claim 11 wherein the total weight of solids (wt % total solids) in the spray dried solution is between 2-15% wt.

13. The solid dispersion of claim 11 wherein the spray drying solvent comprises dichloromethane, or comprises dichloromethane and methanol, or comprises dichloromethane and methanol in a weight to weight ratio of about 85:15, 80:20, 75:25, 70:30, or about 65:35 wt/wt %.

14. The solid dispersion of claim 11 wherein the spray dried dispersion yield is from about 50-100%.

15. A method of preparing a pharmaceutical composition in the form of a tablet comprising the steps of:
(i) preparing a solid dispersion comprising a compound of formula (I) in a substantially amorphous form:

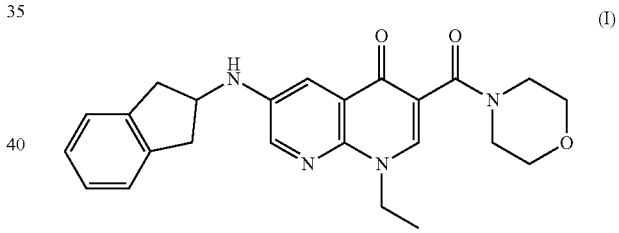

or a salt;
by dispersing said compound of formula (I) within a polymer matrix formed by at least one pharmaceutically acceptable polymer;
(ii) mixing said solid dispersion from step (i) with at least one pharmaceutically acceptable excipient;
(iii) subjecting the resultant mixture from step (ii) to dry granulation; and
(iv) tabletting the dry granulation mixture of step (iii) by compression;
wherein the pharmaceutically acceptable polymer is a crystallization inhibitor polymer which is a hydroxypropyl methylcellulose acetate succinate (HPMCAS), and wherein the ratio of the compound of formula (I) or a salt thereof: crystallization inhibitor polymer is from 30:70 to 70:30 based on wt/wt % of the total solid dispersion,
and wherein the solid dispersion comprises 50 mg-500 mg of the compound of formula (I) or salt thereof.

* * * * *